US009181560B2

(12) United States Patent
Mroczka et al.

(10) Patent No.: US 9,181,560 B2
(45) Date of Patent: Nov. 10, 2015

(54) CHIMERIC PROMOTERS AND THEIR USES THEREOF IN PLANTS

(75) Inventors: Andrew M. Mroczka, Davis, CA (US); Monica P. Ravanello, Fairfield, CA (US); Toni Voelker, Davis, CA (US); Nicholas W. Wagner, Sacramento, CA (US)

(73) Assignee: Monsanto Technology LLC, St. Louis, MO (US)

( * ) Notice: Subject to any disclaimer, the term of this patent is extended or adjusted under 35 U.S.C. 154(b) by 933 days.

(21) Appl. No.: 12/933,086

(22) PCT Filed: Mar. 17, 2009

(86) PCT No.: PCT/US2009/037403
§ 371 (c)(1),
(2), (4) Date: Dec. 14, 2010

(87) PCT Pub. No.: WO2009/117417
PCT Pub. Date: Sep. 24, 2009

(65) Prior Publication Data
US 2011/0119793 A1 May 19, 2011

Related U.S. Application Data

(60) Provisional application No. 61/037,126, filed on Mar. 17, 2008.

(51) Int. Cl.
*C12N 15/82* (2006.01)

(52) U.S. Cl.
CPC .................................. *C12N 15/8234* (2013.01)

(58) Field of Classification Search
None
See application file for complete search history.

(56) References Cited

U.S. PATENT DOCUMENTS

| 5,420,034 | A | 5/1995 | Kridl et al. | |
| 5,599,670 | A | 2/1997 | Jefferson | |
| 5,608,152 | A * | 3/1997 | Kridl et al. | 800/306 |
| 5,723,595 | A | 3/1998 | Thompson et al. | |
| 6,555,673 | B1 * | 4/2003 | Bowen et al. | 536/24.1 |
| 7,053,267 | B2 * | 5/2006 | Knauf et al. | 800/281 |
| 7,166,771 | B2 * | 1/2007 | Eenennaam et al. | 800/298 |
| 2004/0126845 | A1 * | 7/2004 | Eenennaam et al. | 435/69.1 |

FOREIGN PATENT DOCUMENTS

| WO | WO 96/06936 | * | 3/1996 |
| WO | WO 98/46776 A2 | | 10/1998 |

OTHER PUBLICATIONS

Komarnytsky and Borisjuk, Genetic Engin 25:113-41 (2003).*
Ellerstrom, Plant Mol Biol 32:1019-27 (1996).*
Radke et al., Theor Appl Genet 75:685-94 (1988).*
Riethoven_Meth Mol Biol_574_33_2010.*
Potenz_In Vitro Cell Dev Biol Plant_40_1_2004.*
Anjum_Envir Pollut_21_1_2012.*
Shewry_Seed Proteins_563-86_1999.*
Wanasundara, Crit Rev Food Sci & Nutrit 51:635-77 (2011).*
Shewry et al., Plant Cell 7:945-56 (1995).*
Ericson et al., Eur J Biochem 197:741-46 (1991).*
Benfey_EMBO J_9_1685-96_1990.*
van der Geest_Plant Mol Biol_32_579-88_1996.*
Ludwig_PLoS Biol_3_4_588-98_2005.*
Ezcurra_Plant J_24_57-66_2000.*
da Silva Concelcao et al., "A cotyledon regulatory region is responsible for the different spatial expression patterns of *Arabidopsis* 2S albumin genes," *The Plant J.*, 5(4):493-505, 1994.
Ellerstrom et al., "Functional dissection of a napin gene promoter: identification of promoter elements required for embryo and endosperm-specific transcription," *Plant Mol. Biol.*, 32:1019-1027, 1996.
Ericson et al., "Analysis of the promoter region of napin genes from *Brassica napus* demonstrates binding of nuclear protein in vitro to a conserved sequence motif," *Eur. J. Biochem.*, 197:741-746, 1991.
GenBank Accession No. AF302261, dated Oct. 9, 2000.
GenBank Accession No. AF403424, dated Aug. 13, 2001.
GenBank Accession No. AF420598, dated Oct. 23, 2001.
GenBank Accession No. AL035680, dated Nov. 14, 2006.
GenBank Accession No. AL161566, dated Nov. 14, 2006.
GenBank Accession No. AY080779, dated Sep. 18, 2002.
GenBank Accession No. AY117157, dated Sep. 18, 2002.
GenBank Accession No. AY570242, dated Mar. 24, 2004.
GenBank Accession No. AY570249, dated Mar. 24, 2004.
GenBank Accession No. AY570250, dated Mar. 24, 2004.
GenBank Accession No. BT002073, dated Nov. 19, 2002.
GenBank Accession No. BT006557, dated Apr. 25, 2003.
GenBank Accession No. BX826477, dated Feb. 6, 2004.
GenBank Accession No. EF627523, dated Jun. 25, 2007.
GenBank Accession No. EU416279, dated Feb. 25, 2008.
GenBank Accession No. EU723261, dated Jun. 8, 2008.
GenBank Accession No. FJ362599, dated Nov. 26, 2008.
GenBank Accession No. FJ362600, dated Nov. 26, 2008.
GenBank Accession No. FJ362601, dated Nov. 26, 2008.
GenBank Accession No. FJ362602, dated Nov. 26, 2008.
GenBank Accession No. FJ821003, dated Apr. 21, 2009.
GenBank Accession No. FN807060, dated Apr. 21, 2010.
GenBank Accession No. HM027884, dated Jun. 1, 2010.
GenBank Accession No. J02586, dated Apr. 27, 1993.
GenBank Accession No. J02782, dated Apr. 27, 1993.
GenBank Accession No. J02798, dated Oct. 11, 2001.
GenBank Accession No. K01545, dated Apr. 27, 1993.
GenBank Accession No. M22034, dated Apr. 27, 1993.
GenBank Accession No. M22035, dated Apr. 27, 1993.
GenBank Accession No. M64632, dated Aug. 13, 1993.

(Continued)

*Primary Examiner* — Medina A Ibrahim
*Assistant Examiner* — Russell Boggs
(74) *Attorney, Agent, or Firm* — Dentons US LLP; Carine M. Doyle, Esq.

(57) ABSTRACT

The present invention provides novel promoters for use in plants. Specifically, the present invention provides novel enhanced plant promoters. The present invention also provides DNA constructs; transgenic cells, plants, and seeds containing these novel promoters; and methods for preparing and using the same.

12 Claims, 3 Drawing Sheets

(56) References Cited

OTHER PUBLICATIONS

GenBank Accession No. M64633, dated Aug. 13, 1993.
GenBank Accession No. U04943, dated Nov. 29, 1995.
GenBank Accession No. U04944, dated Nov. 29, 1995.
GenBank Accession No. U04945, dated Nov. 29, 1995.
GenBank Accession No. X14492, dated Apr. 18, 2005.
GenBank Accession No. X17542, dated Oct. 23, 2008.
GenBank Accession No. X58142, dated Apr. 18, 2005.
GenBank Accession No. X67833, dated Sep. 4, 1997.
GenBank Accession No. X70333, dated Dec. 7, 1993.
GenBank Accession No. Y13108, dated May 14, 1997.
GenBank Accession No. Z24744, dated Apr. 18, 2005.
GenBank Accession No. Z24745, dated Apr. 18, 2005.
Kim et al., "Seed-specific expression of sesame microsomal oleic acid desaturase is controlled by combinatorial properties between negative cis-regulatory elements in the SeFAD2 promoter and enhancers in the 5'-UTR . . . ," *Mol. Gen. Genom.*, 276:351-368, 2006.
Koncz et al., "The promoter of TL-DNA gene 5 controls the tissue-specific expression of chimaeric genes carried by a novel type of *Agrobacterium* binary vector," Mol. Gen. Genet., 204:383-396, 1986.
NCBI Accession No. NM_118849, dated Aug. 21, 2009.
NCBI Accession No. NM_118850, dated Aug. 21, 2009.
PCT International Search Report for Application No. PCT/US2009/037403, dated Feb. 11, 2009.
Radke et al., "Transformation and regeneration of *Brassica rapa* using *Agrobacterium tumefaciens*," Plant Cell Rep., 11:499-505, 1992.
Thomas et al., "Identification of an enhancer element for the endosperm-specific expression of high molecular weight glutenin," *The Plant Cell*, 2:1171-1180, 1990.
van der Geest et al., "A 68 by element of the β-phaseolin promoter functions as a seed specific enhancer," *Plant Mol. Biol.*, 32:579-588, 1996.

* cited by examiner

```
                         SEQUENCE LISTING

<160> NUMBER OF SEQ ID NOS: 37

<210> SEQ ID NO 1
<211> LENGTH: 825
<212> TYPE: DNA
<213> ORGANISM: Artificial sequence
<220> FEATURE:
<223> OTHER INFORMATION: Chimeric promoter sequence using enhancer from
      Brassica rapa

<400> SEQUENCE: 1
ctgatacaca cttaagcatc atgtggaaag ccaaagacaa ttggagcgag actcagggtc      60
gtcataatac caatcaaaga cgtaaaacca gacgcaacct ctttggttga atgtaatgaa     120
agggatgtgt cttggtatgt atgtacgaat aacaaaagag aagatggaat tagtagtaga     180
aatatttggg agctttttaa gcccttcaag tgtgcttttt atcttattga tatcatccat     240
ttgcgttgtt taatgcgtct ctagatatgt tcctatatct ttctcagtgt ctgataagtg     300
aaatgtgaga aaaccatacc aaaccaaaat attcaaatct tatttttaat aatgttgaat     360
cactcggagt tgccaccttc tgtgccaatt gtgctgaatc tatcacacta gaaaaaaaca     420
tttcttcaag gtaatgactt gtggactatg ttctgaattc tcattaagtt tttattttct     480
gaagtttaag tttttaccct ctgttttgaa atatatcgtt cataagatgt cacgccagga     540
catgagctac acatcgcaca tagcatgcag atcaggacga tttgtcactc acttcaaaca     600
cctaagagct tctctctcac agcgcacaca catatgcatg caatatttac acgtgatcgc     660
catgcaaatc tccattctca cccaggacga tttgtcactc acttcaaaca cctaagagct     720
tctctctcac agcgcacaca catatgcatg caatatttac acgtgatcgc catgcaaatc     780
tccattctca cctataaatt agagcctcgg cttcactctt tactc                     825

<210> SEQ ID NO 2
<211> LENGTH: 929
<212> TYPE: DNA
<213> ORGANISM: Artificial Sequence
<220> FEATURE:
<223> OTHER INFORMATION: Chimeric promoter sequence using enhancer from
      Brassica rapa

<400> SEQUENCE: 2
ctgatacaca cttaagcatc atgtggaaag ccaaagacaa ttggagcgag actcagggtc      60
gtcataatac caatcaaaga cgtaaaacca gacgcaacct ctttggttga atgtaatgaa     120
agggatgtgt cttggtatgt atgtacgaat aacaaaagag aagatggaat tagtagtaga     180
aatatttggg agctttttaa gcccttcaag tgtgcttttt atcttattga tatcatccat     240
ttgcgttgtt taatgcgtct ctagatatgt tcctatatct ttctcagtgt ctgataagtg     300
aaatgtgaga aaaccatacc aaaccaaaat attcaaatct tatttttaat aatgttgaat     360
cactcggagt tgccaccttc tgtgccaatt gtgctgaatc tatcacacta gaaaaaaaca     420
tttcttcaag gtaatgactt gtggactatg ttctgaattc tcattaagtt tttattttct     480
gaagtttaag tttttaccct ctgttttgaa atatatcgtt cataagatgt cacgccagga     540
catgagctac acatcgcaca tagcatgcag atcaggacga tttgtcactc acttcaaaca     600
cctaagagct tctctctcac agcgcacaca catatgcatg caatatttac acgtgatcgc     660
```

```
catgcaaatc tccattctca cctttttatt ttctgaagtt taagtttta ccttctgttt    720 tgaaatatat cgttcataag atgtcacgcc aggacatgag ctacacatcg cacatagcat    780
gcagatcagg acgatttgtc actcacttca aacacctaag agcttctctc tcacagcgca    840
cacacatatg catgcaatat ttacacgtga tcgccatgca aatctccatt ctcacctata    900
aattagagcc tcggcttcac tctttactc                                      929
```

```
<210> SEQ ID NO 3
<211> LENGTH: 866
<212> TYPE: DNA
<213> ORGANISM: Artificial Sequence
<220> FEATURE:
<223> OTHER INFORMATION: Chimeric promoter sequence using enhancer from
      Brassica rapa

<400> SEQUENCE: 3
ctgatacaca cttaagcatc atgtggaaag ccaaagacaa ttggagcgag actcagggtc     60
gtcataatac caatcaaaga cgtaaaacca gacgcaacct ctttggttga atgtaatgaa    120
agggatgtgt cttggtatgt atgtacgaat aacaaaagag aagatggaat tagtagtaga    180
aatatttggg agcttttttaa gcccttcaag tgtgctttttt atcttattga tatcatccat   240
ttgcgttgtt taatgcgtct ctagatatgt tcctatatct ttctcagtgt ctgataagtg    300
aaatgtgaga aaaccatacc aaaccaaaat attcaaatct tattttaat aatgttgaat     360 cactcggagt tgccaccttc tgtgccaatt gtgctgaatc tatcacacta gaaaaaaaca    420
tttcttcaag gtaatgactt gtggactatg ttctgaattc tcattaagtt tttatttct    480 gaagtttaag ttttaccctt ctgttttgaa atatatcgtt cataagatgt cacgccagga    540
catgagctac acatcgcaca tagcatgcag atcaggacga tttgtcactc acttcaaaca    600
cctaagagct tctctctcac agcgcacaca catatgcatg caatatttac acgtgatcgc    660
catgcaaatc tccattctca cccaggacga tttgtcactc acttcaaaca cctaagagct    720
tctctctcac agcgcacaca catatgcatg caatatttac acgtgatcgc catgcaaatc    780
tccattctca cctataaatt agagcctcgg cttcactctt tactcaaacc aaaactcatc    840
actacagaac atacacaaga taattc                                         866
```

```
<210> SEQ ID NO 4
<211> LENGTH: 970
<212> TYPE: DNA
<213> ORGANISM: Artificial Sequence
<220> FEATURE:
<223> OTHER INFORMATION: Chimeric promoter sequence using enhancer from
      Brassica rapa

<400> SEQUENCE: 4
ctgatacaca cttaagcatc atgtggaaag ccaaagacaa ttggagcgag actcagggtc     60
gtcataatac caatcaaaga cgtaaaacca gacgcaacct ctttggttga atgtaatgaa    120
agggatgtgt cttggtatgt atgtacgaat aacaaaagag aagatggaat tagtagtaga    180
aatatttggg agcttttttaa gcccttcaag tgtgctttttt atcttattga tatcatccat   240
ttgcgttgtt taatgcgtct ctagatatgt tcctatatct ttctcagtgt ctgataagtg    300
aaatgtgaga aaaccatacc aaaccaaaat attcaaatct tattttaat aatgttgaat     360 cactcggagt tgccaccttc tgtgccaatt gtgctgaatc tatcacacta gaaaaaaaca    420
tttcttcaag gtaatgactt gtggactatg ttctgaattc tcattaagtt tttatttct    480 gaagtttaag ttttaccctt ctgttttgaa atatatcgtt cataagatgt cacgccagga    540
```

```
catgagctac acatcgcaca tagcatgcag atcaggacga tttgtcactc acttcaaaca    600
cctaagagct tctctctcac agcgcacaca catatgcatg caatatttac acgtgatcgc    660
catgcaaatc tccattctca cctttttatt ttctgaagtt taagttttta ccttctgttt    720
tgaaatatat cgttcataag atgtcacgcc aggacatgag ctacacatcg cacatagcat    780
gcagatcagg acgatttgtc actcacttca aacacctaag agcttctctc tcacagcgca    840
cacacatatg catgcaatat ttacacgtga tcgccatgca aatctccatt ctcacctata    900
aattagagcc tcggcttcac tctttactca aaccaaaact catcactaca gaacatacac    960
aagataattc                                                           970
```

<210> SEQ ID NO 5
<211> LENGTH: 41
<212> TYPE: DNA
<213> ORGANISM: Artificial Sequence
<220> FEATURE:
<223> OTHER INFORMATION: Chimeric promoter sequence using enhancer from
      Brassica rapa

<400> SEQUENCE: 5

```
aaaccaaaac tcatcactac agaacataca caagataatt c                         41
```

<210> SEQ ID NO 6
<211> LENGTH: 756
<212> TYPE: DNA
<213> ORGANISM: Brassica rapa

<400> SEQUENCE: 6

```
ctgatacaca cttaagcatc atgtggaaag ccaaagacaa ttggagcgag actcagggtc     60
gtcataatac caatcaaaga cgtaaaacca gacgcaacct ctttggttga atgtaatgaa    120
agggatgtgt cttggtatgt atgtacgaat aacaaaagag aagatggaat tagtagtaga    180
aatatttggg agcttttttaa gcccttcaag tgtgctttttt atcttattga tatcatccat    240
ttgcgttgtt taatgcgtct ctagatatgt tcctatatct ttctcagtgt ctgataagtg    300
aaatgtgaga aaaccatacc aaaccaaaat attcaaatct tatttttaat aatgttgaat    360
cactcggagt tgccaccttc tgtgccaatt gtgctgaatc tatcacacta gaaaaaaaca    420
tttcttcaag gtaatgactt gtggactatg ttctgaattc tcattaagtt tttattttct    480
gaagtttaag tttttacctt ctgttttgaa atatatcgtt cataagatgt cacgccagga    540
catgagctac acatcgcaca tagcatgcag atcaggacga tttgtcactc acttcaaaca    600
cctaagagct tctctctcac agcgcacaca catatgcatg caatatttac acgtgatcgc    660
catgcaaatc tccattctca cctataaatt agagcctcgg cttcactctt tactcaaacc    720
aaaactcatc actacagaac atacacaaga taattc                              756
```

<210> SEQ ID NO 7
<211> LENGTH: 715
<212> TYPE: DNA
<213> ORGANISM: Brassica rapa

<400> SEQUENCE: 7

```
ctgatacaca cttaagcatc atgtggaaag ccaaagacaa ttggagcgag actcagggtc     60
gtcataatac caatcaaaga cgtaaaacca gacgcaacct ctttggttga atgtaatgaa    120
agggatgtgt cttggtatgt atgtacgaat aacaaaagag aagatggaat tagtagtaga    180
aatatttggg agcttttttaa gcccttcaag tgtgctttttt atcttattga tatcatccat    240
```

```
ttgcgttgtt taatgcgtct ctagatatgt tcctatatct ttctcagtgt ctgataagtg      300
aaatgtgaga aaaccatacc aaaccaaaat attcaaatct tattttttaat aatgttgaat     360 cactcggagt tgccaccttc tgtgccaatt gtgctgaatc tatcacacta gaaaaaaaca     420
tttcttcaag gtaatgactt gtggactatg ttctgaattc tcattaagtt tttattttct      480
gaagtttaag ttttacctt ctgttttgaa atatatcgtt cataagatgt cacgccagga      540
catgagctac acatcgcaca tagcatgcag atcaggacga tttgtcactc acttcaaaca     600
cctaagagct tctctctcac agcgcacaca catatgcatg caatatttac acgtgatcgc     660
catgcaaatc tccattctca cctataaatt agagcctcgg cttcactctt tactc         715
```

<210> SEQ ID NO 8
<211> LENGTH: 1137
<212> TYPE: DNA
<213> ORGANISM: Brassica juncea

<400> SEQUENCE: 8

```
tcttcatcgg tgattgattc cttaaagac ttatgtttct tatcttgctt ctgaggcaag       60
tattcagtta ccagttacca cttatattct tgactttctg actgatcctc attttttccaa   120 cattttaaat ttcactattg gctgaatgct tcttctttga ggagaaaaca attcagatgg    180
cagaaatgta tcaaccaatg catatataca aatgtacctc ttgttctcaa acatctatc     240 ggatggttcc atttgctttg tcatccaatt agtgactact ttatattatt cactcctctt    300
tattactatt tcatgcgag gttgccatgt acattatatt tgtaaggatt gacgctattg    360 agcgttttttc ttcaattttc tttatttaag acatgggtat gaaatgtgtg ttagagttgg   420
gttgaatgag atatacgttc aagtgaagtg gcataccgtt ctcgagtaag gatgacctac   480
ctattcttga gacaaatgtt acatttttagt atcagagtaa aatgtgtacc tataactcaa  540
attcgattga catgtatcca ttcaacataa aattaaaccaa gcctgcactc gcatccacat    600
ttcaagatat ttttcaaacc gttcggctcc tatccaccgg gtgtaacaag acggattccg   660
aatttggagg attttgactc aaattcccaa tttatattga ccgtgactaa atcaacttta    720
acttctataa ttctgattaa gctcccaatt tatattccca acggcactac ctccaaaatt    780
tatatagact ctcatcccct tttaaaccaa cttagtaaac gtttttttttt ttaattttat   840 gaagttaagt ttttaccttg ttttttaaaaa gaatcgttca taagatgcca tgccagaaca   900
ttagctacac gttacacata gcatgcagcc gcggagaatt gttttttcttc gccacttgtc    960 actcccttca aacacctaag agcttctctc tcacacgaca cacatacaat cacatgcgtg   1020
catgcattat tacacgtgat cgccatgcaa atctccttta tagcctataa attaactcat   1080
ccgcttcact ctttactcaa accaaaactc atcaatacaa acaagattaa aaacata      1137
```

<210> SEQ ID NO 9
<211> LENGTH: 1147
<212> TYPE: DNA
<213> ORGANISM: Brassica napus

<400> SEQUENCE: 9

```
aagctttctt catcggtgat tgattccttt aaagacttat gtttcttatc ttgcttctga      60
ggcaagtatt cagttaccag ttaccactta tattctggac tttctgactg catcctcatt    120
tttccaacat tttaaatttc actattggct gaatgcttct tctttgagga agaaacaatt    180
cagatggcag aaatgtatca accaatgcat atatacaaat gtacctcttg ttctcaaaac   240
```

```
atctatcgga tggttccatt tgctttgtca tccaattagt gactacttta tattattcac    300
tcctctttat tactattttc atgcgaggtt gccatgtaca ttatatttgt aaggattgac    360
gctattgagc gttttcttc aattttcttt attttagaca tgggtatgaa atgtgtgtta    420
gagttgggtt gaatgagata tacgttcaag cgaatggcat accgttctcg agtaaggatg    480
acctacccat tcttgagaca aatgttacat tttagtatca gagtaaaatg tgtacctata    540
actcaaattc gattgacatg tatccattca acataaaatt aaaccagcct gcacctgcat    600
ccacatttca agtattttca aaccgttcgg ctcctatcca ccgggtgtaa caagacggat    660
tccgaatttg gaagattttg actcaaattc ccaatttata ttgaccgtga ctaaatcaac    720
tttaacttct ataattctga ttaagctccc aatttatatt cccaacggca ctacctccaa    780
aatttataga ctctcatccc cttttaaacc aacttagtaa acgttttttt ttttaatttt    840
atgaagttaa gttttttacct tgttttttaaa aagaatcgtt cataagatgc cacgccagaa    900
cattagctac atgttacaca tagcatgcag ccgcggagaa ttgttttct tcgccacttg     960 tcactcccct caaacaccta agagcttctc tctcacagca cacacataca atcacatgcg   1020
tgcatgcatt attacacgtg atcgccatgc aaatctcctt tatagcctat aaattaactc   1080
atccgcttca ctctttactc aaaccaaaac tcatcaatac aaacaagatt aaaaacatac   1140
aggatcc                                                             1147

<210> SEQ ID NO 10
<211> LENGTH: 3289
<212> TYPE: DNA
<213> ORGANISM: Brassica napus

<400> SEQUENCE: 10
aagctttctt catcggtgat tgattccttt aaagacttat gtttcttatc ttgcttctga     60
ggcaagtatt cagttaccag ttaccactta tattctggac tttctgactg catcctcatt    120
tttccaacat tttaaatttc actattggct gaatgcttct tctttgagga agaaacaatt    180
cagatggcag aaatgtatca accaatgcat atatacaaat gtacctcttg ttctcaaaac    240
atctatcgga tggttccatt tgctttgtca tccaattagt gactacttta tattattcac    300
tcctctttat tactattttc atgcgaggtt gccatgtaca ttatatttgt aaggattgac    360
gctattgagc gttttcttc aattttcttt attttagaca tgggtatgaa atgtgtgtta    420
gagttgggtt gaatgagata tacgttcaag tgaagtggca taccgttctc gagtaaggat    480
gacctaccca ttcttgagac aaatgttaca ttttagtatc agagtaaaat gtgtacctat    540
aactcaaatt cgattgacat gtatccattc aacataaaat taaaccagcc tgcacctgca    600
tccacatttc aagtattttc aaaccgttcg gctcctatcc accgggtgta acaagacgga    660
ttccgaattt ggaagatttt gactcaaatt cccaatttat attgaccgtg actaaatcaa    720
ctttaacttc tataattctg attaagctcc caatttatat cccaacggca ctacctcca    780 aaatttatag actctcatcc ccttttaaac caacttagta acgttttttt ttttaatttt    840
tatgaagtta agttttttacc ttgttttttaa aaagaatcgt tcataagatg ccatgccaga   900
acattagcta cacgttacac atagcatgca gccgcggaga attgttttc ttcgccactt     960 gtcactccct tcaaacacct aagagcttct ctctcacagc acacacatac aatcacatgc   1020
gtgcatgcat tattacacgt gatcgccatg caaatctcct ttatagccta taaattaact   1080
catccgcttc actctttact caaaccaaaa ctcatcaata caaacaagat taaaaacata   1140
cacgaatggc gaacaagctc ttcctcgtct cggcaactct cgccttcttc ttccttctca   1200
```

```
ccaatgcctc catctaccgg acggtcgtcg agttcgacga agatgatgcc acagactcag    1260
ccggcccatt taggattcca aaatgtagga aggagtttca gcaagcacaa cacctaagag    1320
cttgccagca gtggctccac aagcaagcaa tgcagtctgg cggtggtcct agctggaccc    1380
tcgacggtga gtttgacttt gaagacgaca tggagaaccc gcagggtcca cagcagagac    1440
cgcctctact ccagcagtgc tgtaacgagc tccaccagga agagcccctt gcgtttgcc     1500 caaccttgaa aggagcatcc aaagcggtta acaacaaat tcaacaacag gacaacagc      1560 aaggaaagca gcaaatggtg agccgtatct accagaccgc tacgcactta cctaaagttt    1620
gcaacatccc gcaagttagc gtttgtccct tccagaagac catgcctggg ccctcctact    1680
agattccaaa cgaaaccctc gagtgtatga atgtggttgt cgatatatgt caacaccaca    1740
cctcatcgcg tgtttcataa taatatgtaa ggttttatct aggatgtttg aggctaatgt    1800
aaaattagca ctactccata ataaaagaga ggctcttaat gtttaattta ctcgatcaat    1860
catcttagtt aactcgtaca tgggcttta acggcaagcg aaacaccgtt caaactgctc     1920
tgtgactgtt ctctatcaat cacatataga ttttaagttg cttttatttt cccccatagg    1980
catcggtgta gagaaacaac tggcgtgtct ccatattgac gactacaaat ttgcaactag    2040
ttctagcttg ttttcaacta ttggaagatc attttacatg aactcaacgt gttaattagc    2100
tctttgttat ccacaagaaa taacacacat gcatgatcaa gaggaagaga catggaaaaa    2160
gtaaaattta cattaacaac ggtttctttt tctcctctct tcttccttat cttcatctat    2220
tgtctatgct ctcgagttgt ctatgctcga gcaactagcc caactagcct acacctctct    2280 ccctttccc aagcaaccaa ttttctgca tgtcaccaac taatacatcg ctatatagag      2340
ctacataaca cccaactaag tttctctcta cgcatccaca acaaccacat cagccacgcg    2400
ccattctcaa gaaattatat ttctttcttt cgctagagct atatatagca gacaaatccc    2460
tttgtctgag atgcaaatgg ttacacacag ctaaaggaat aattgggtgt gaatttgaca    2520
tttcaccaaa aggttaccat ttgaattaaa aaatagttgc gagttgcaaa taattcaacc    2580
aactctgttg aaagaaaaaa aagactgaat ttgttaagat tgatgttttt gttttgatgt    2640
ttttgttata aatggtaacc ttttggagc taccttatcc actatttggt atgaaatgaa     2700
tgggagaagg catggtgaaa cgccaaaggc cacatccgta ttggtcgctc gcatcgacaa    2760
gctggttagg aatcgaataa ccagtttgag aatgttggat gctcgaaagt ataacaaggc    2820
catggaaact tggttctcct acagatgatt ctttgttttc tgtctctgtt ttccttttt     2880 caaaacattc agttaatgta acagtctgta caaaaaaatt tttgaataaa tttaacatta    2940
tttcaaaaaa gaaaaggtaa cttttttgga gaaatgcctc gattgatgtt tttgttttgt    3000
tgaagtttga gtaatgaaat tgagtgttgc tgatttgttt agtctctcat tttttccatt    3060
tattggtacg gttttatttt attttatttt attttatttt ttatttttt tgattcattc     3120 aaaaaaacct gtatacatca agtgcatcat ttgtttctat aaagaaaact caagatcaac    3180
taccctcccc ttcttacata ttagcttcct ttttacattc tagtaagaaa ccaaaattgc    3240
atcagttgct ccatacccctt cacctcatcc attctcatca aagagatct                3289
```

<210> SEQ ID NO 11
<211> LENGTH: 1257
<212> TYPE: DNA
<213> ORGANISM: Brassica napus

<400> SEQUENCE: 11

-continued

```
gttcggctcc taccaccggg tgtaacaaga cggattccga atttggaaga ttttgactca      60
aattcccaat ttatattgac cgtgactaaa tcaactttaa cttctataat tctgattaag     120
ctctcccaat ttatattccc aacggcacta cctccaaaat ttttagactc tcgtcccctt     180
ttaaaccaac ttactaaacg tttttttttt aatttatgaa gttaagtttt taccttgttt     240
ttaaaaagaa tcgctcataa gatgccatgc agaacatta gctacacgtt acacaaagca     300
tgcagacgcg gaggattgtt tttgttcgtc acttgtcact cccttcaaac acctaagagc     360
ttctctctca cagcacacac atacaatcac atgcgtgcat gcattattac acgtgatcgc     420
catgcaaatc tcctttatca cctataaatt aactcatccg cttaactctt tactcaaacc     480
aaaactcatc aatacaaaca agattaaaaa catacactaa tggcgaacaa gctcttcctc     540
gtctcggcaa ctctcgcctt cttcttcctt ctcaccaatg cctccatcta ccggacggtg     600
gtcgagttcg acgaagatga tgcaacaaac ccagccggcc catttaggat tccaaaatgt     660
aggaaggagt ttcagcaagc acaacaccta aaagcttgcc agcagtggct ccacaagcaa     720
gcaatgcagt ctggcagtgg tcctagctgg accctcgacg tgagtttga ctttgaagac     780
gacatggaga accccaggg tccacagcag agaccgcctc tactccagca gtgctgtaac     840
gagctccacc aggaagagcc cctttgcgtt tgcccaacct tgaaaggagc atccaaagcg     900
gttaaacaac aaattcagca acagggacaa cagcaaggaa agctgcaaat ggtgagccgt     960
atctaccaga cagctactca cttacctaaa gtttgcaaaa tcccgcaagt tagcgtatgt    1020
ccttccaga agaccatgcc tgggccctcc tactagattc caaacgaaac cctcgagtgt    1080
atgaatgtgg ttgtcgatat atgtcaacac cacacctcat cgcgtgtttc ataataatat    1140
gtaaggtttt atctaggatg tttgaggcta atgtaaaatt agcactactc cataataaaa    1200
gagaggctct taatgtttaa tttacttgat caatcatctt aactcgtaca caggccg      1257
```

<210> SEQ ID NO 12
<211> LENGTH: 1993
<212> TYPE: DNA
<213> ORGANISM: Brassica napus

<400> SEQUENCE: 12

```
aagctttctt catcggtgat tgattccttt aaagacttat gtttcttatc ttgcttctga      60
ggcaagtatt cagttaccac ttatattctg gactttctga ctgcatcctc attttttccaa    120
cattttaaat ttcactattg gctgaatgct tcttctttga ggaagaaaca attcagatgg     180
cagaaatgta tcaaccaatg catatataca aatgtacctc ttgttctcaa acatctatc     240
ggatggttcc atttgctttg tcatccaatt agtgactact ttatattatt cactcctctt     300
tattactatt tcatgcgag gttgccatgt acattatatt tgtaaggatt gacgctattg     360
agcgttttc ttcaattttc tttattttag acatgggtat gaaatggttg ttagagttgg     420
gttgaatgag atatacgttc aagtgaatgg cataccgttc tcgagtaagg atgacctacc     480
cattcttgag acaaatgtta catttttagta tcagagtaaa atgtgtacct ataactcaaa    540
ttcgattgac atgtatccat tcaacataaa attaaccag cctgcacctg catccacatt     600
tcaagtattt tcaaaccgtt cggctcctat ccacgggtg taacaagacg gattccgaat     660
ttggaagatt ttgactcaaa ttcccaattt atattgaccg tgactaaatc aactttaact     720
tctataattc tgattaagct cccaattat attcccaacg gcactacctc caaaatttat     780
agactctcat cccccttttaa accaacttag taaacgtttt ttttttttaat tttatgaagt    840
taagttttta ccttgttttt aaaagaatc gttcataaga tgccatgcca gaacattagc     900
```

```
tacacgttac acatagcatg cagccgcgga gaattgtttt tcttcgccac ttgtcactcc      960
cttcaaacac ctaagagctt ctctctcaca gcacacacat acaatcacat gcgtgcatgc     1020
attattacac gtgatcgcca tgcaaatctc ctttatagcc tataaattaa ctcatccgct     1080
tcactcttta ctcaaaccaa aactcatcaa tacaaacaag attaaaaaca tacacgaatg     1140
gcgaacaagc tcttcctcgt ctcggcaact ctcgccttct tcttccttct caccaatgcc     1200
tccatctacc ggacggtcgt cgagttcgac gaagatgatg ccacaaactc agccggccca     1260
tttaggattc caaaatgtag gaaggagttt cagcaagcac aacacctaag agcttgccag     1320
cagtggctcc acaagcaagc aatgcagtct ggcggtggtc ctagctggac cctcgacggt     1380
gagtttgact ttgaagacga catggagaac ccgcagggtc cacagcagag accgcctcta     1440
ctccagcagt gctgtaacga gctccaccag gaagagcccc tttgcgtttg cccaaccttg     1500
aaaggagcat ccaaagcggt taaacaacaa attcaacaac agggacaaca gcaaggaaag     1560
cagcaaatgg tgagccgtat ctaccagacc cgtacgaact tacctaaagt ttgcaacatc     1620
ccgcaagtta gcgtttgtcc cttccagaag accatgcctg ggcctccta  ctagattcca     1680 aacgaaaccc tcgagtgtat gaatgtggtt gtcgatatat gtcaacacca cacctcatcg     1740
cgtgtttcat aataatatgt aaggttttat ctaggatgtt tgaggctaat gtaaaattag     1800
cactactcca aataaaaga gaggctctta atgtttaatt tactcgatca atcatcttag     1860
ttaactcgta catgggcttt taacggcaag cgaaacaccg ttcaaactgc tctgtgactg     1920
ttctctatca atcacatata gattttaagt tgcttttatt ttcccccata ggcatcggtg     1980
tagagaaaca act                                                       1993
```

<210> SEQ ID NO 13
<211> LENGTH: 1137
<212> TYPE: DNA
<213> ORGANISM: Brassica oleracea

<400> SEQUENCE: 13

```
tcttcatcgg tgattgattc cttttaaagac ttatgtttct tatcttgctt ctgaggcaag      60
tattcagtta ccactatat tctggacttt ctgactgcat cctcattttt ccaacatttt      120
aaatttcact attggctgaa tgcttcttct tctttgagga agaaacagtt cagatggcag      180
aaatgtatca accaatgcat atatacaaat gtacctcttg ttcttaaaac atctatcgga      240
tggttccatt tgctttgtca tccaattagg tgactacttt atattattca ctcctcttta      300
ttactatttt catgcgaggg ttgccatgta cattatattt ggtaaggatt ggacgctatt      360
gagcgttttt cttcaatttt ctttatttaa gacatgggta tgaatgtgtg ttagagtggg      420
gttggatgag attcccgtca aagtgaattg gcataccgtc cccgggtaag ggtgaccccc      480
catcctgggg aaaatgttac attttagggt actcagggga atggggtccc attactcaaa      540
tccgggggaa atgtttccct tcaacataaa attaaacccg gccggaccgg aatccccaat      600
tcaaggtttt taaccggcct tcgggagcc  cccaaccgga ccggggtcct atccagcggt      660
tgaacaaggg gggttccgga attgggatgg ttttggcccg aattcccaat taaatttgac      720
ccgtataatt ctggttaagc tgccaaatta tatccgaacg gcactacctc caaaatttaa      780
aaagactcta atccctgttt aaacccgaac ttagtaaccg ttttttttgg taattttttg      840
aagttgagtt tttaccttgt tttggaaggg agtcgttcat gagatgccat gccagaacat      900
tagctagccg gttacacata gcatgcagcc gcggaggatt gttttcttc gccacttgtc      960
```

| cctcccttca aacacctaag agcttcttta aaacagccca cacagccaat cacatgcgtg | 1020 |
| catgcattat tacacgtgat cgccatgcaa atctcccctta cgcctataa attaactcat | 1080 |
| ccgcttcact ctttactcaa accaaaactc atcaatacaa acaagattaa aaacata | 1137 |

<210> SEQ ID NO 14
<211> LENGTH: 1026
<212> TYPE: DNA
<213> ORGANISM: Brassica napus

<400> SEQUENCE: 14

| cctcattaag ttttcatttt ttgaagttta agttttacc ttcttttttg aaaaatatcg | 60 |
| ttcataagat gtcacgccag gacatgagct acacatcaca tattagcatg cagatgcgga | 120 |
| cgatttgtca ctcacttcaa acacctaaaa gagcttctct ctcacagcac acacacatat | 180 |
| gcatgcaata tttacacgtg atcgccatgc aaatctccat tctcacctat aaattagagg | 240 |
| ctcggcttca ctttttact caaaccaaaa ctcatcacta caaaacatac acaaatggcg | 300 |
| aacaagctct tcctcgtctc ggcaactctc gccttgttct tccttctcac caatgcctcc | 360 |
| gtctacagga cggttgtgga agtcgacgaa gacgatgcca caaatccagc cggcccattt | 420 |
| aggattccaa aatgtagaaa ggagtttcag caagcacaac acctaagagc ttgccaacaa | 480 |
| tggctccaca agcaggcaat gcagcccggt ggtggtagtg gtccaagctg gactctcgac | 540 |
| ggtgagtttg attttgaaga cgacgtggag aaccaacaac agggcccaca gcagaggcca | 600 |
| ccgccacccc agcagtgctg caacgagctc caccaggaag agccactttg cgtttgccca | 660 |
| accttgaaag gagcatccaa agccgttaga caacaggttc gacaacaaca gggacaacaa | 720 |
| atgcagggac agcagatgca gcaagtaatt agccgtgtct accagactgc tacgcactta | 780 |
| cctagagttt gcaacatcag gcaagttagc atttgtccct tccagaagac catgcctggg | 840 |
| cccggcttct actagattcc aaacgaaata tcctcgagag tgtgtatacc acggtgatat | 900 |
| gagtgtggtt gttgatgtat gttaacacta catagtcatg gtgtgtgttc cataaataat | 960 |
| gtactaatgt actaatgtaa taagaactac tccgtagacc ggtaataaaa gagaagtttt | 1020 |
| tttttt | 1026 |

<210> SEQ ID NO 15
<211> LENGTH: 2084
<212> TYPE: DNA
<213> ORGANISM: Brassica rapa

<400> SEQUENCE: 15

| aagcttattt ctcttttcga cactctaatt gagaccgtgc gctctatcta gaccaattag | 60 |
| aattagatgg agctctaaag gtttgaatgg ctgttttctt gttcatatga ttaacttcta | 120 |
| aacttgtgta taaatattct ctgaaagtga cttcttttag gcatatgtag gttgcatgac | 180 |
| aaaactgagg aagattaacc ttctcaattt aaggaagagg aggaacagcc gaagaagaaa | 240 |
| taagaatagt cagtctgcat ctcatgactc agcttaacgg tcgtcgtcct catgaacaga | 300 |
| tacattttg tcatatacac ttgaaagttc cttcactaac tgtgtaatct tttggtagat | 360 |
| atcactacaa tgtcggagag acaaggctgc gccagcatat acaaaaggga aatgaagatg | 420 |
| gccttttgat tagctgtgta gcatcagcag ctatctctgg gctctcatca tggatgctgg | 480 |
| aactggattc acttctcaag tttatgagtt gtcaccggtc ttcctacaca aggtaataat | 540 |
| cagttgaagc aattaagaat caatttgatt tgtagtaaac taagaagaac ttaccttatg | 600 |
| ttttcccgc aggactggat tatggaacaa tgggaaaaga actactatat aagctccata | 660 |

```
gctggttcag ataacggagc tctttagttg ttatgtcaaa aggttagtgt ttagtgaata    720
ataaacttat taccacaaag tcttcattga cttatttata tacttgttgt gaattgctag    780
gaactactta ttctcagcag tcatacaaag tgagtgactc atttccgttc aagtggataa    840
ataagaaatg gaaagaagat tttcatgtaa cctccatgac aactgctggt aatcgttggg    900
gtgtgggtaa tgtcgaggaa ctctggcttc tctgatcagg taggttttg tctcttaatt    960 gtctggttgt ttttatttc ccctgatagt ctaatatgat aactctgcgt tgtgaaaggt   1020
ggtggagctt gacttttgt acccaagcga tgggatacat aggaggtggg agaatgggta   1080
tagaataaca tcaatggcag caactgcgat caagcagctt catattaagc ataccaaagc   1140
gtaagaatgg tggatgaaac tcaagagact ctccgcacca ccgcctttcc aagtactcat   1200
gtcaaaggtt ggtttcttta gctttgaaca cagatttgga tctttttgtt ttgtttccat   1260
atacttagga cctgagagct tttggttctc gagattcccg tcaaagtgaa ttgcataccg   1320
ttctctagta agatgaccta ccattcattc ttgagacaaa tgttacattt tagtatcaga   1380
gtaaaatgtg tacctataac tcaaattcag tattgacaat gtatccattc aaactataaa   1440
attaaaccag cctgcactcg catccacatt tcaagtattt tcaaacgttc ggctcctatc   1500
caccgggtgt aacaagacgg atatcgaatt tggaggattt tgactcaaat tcccaattta   1560
tattgaccgt gactaaatca actttaactt ctataattct gattaagctc caatttata    1620 ttccgaacgg cactaccaaa ccaatatatt caatcttatt ttatataatg ttcaatcagt   1680
cggagttgcc accttctgtg ccaattgtgc tgaatctatc acactagaaa aaacattctt   1740
caaggtaatg acttgtggac tatgttctga cttctcatta agtttttatt ttcgcgaagt   1800
taagttttta ccttctgttt tgaaatatat cgttcataac atcgttctca cgccaggacc   1860
attgcagcta cataccattg cagcatctac cattcgccat gcaatgcaga tcaggacgat   1920
ttgtcactca cttcaaacac ctaagagctt ctctctcaca cgcacacac atatgcatgc   1980 aatattacac gtgatgcatg caaatctcca ttcttcacct ataaattaga gcctcggctt   2040
cactctttac tcaaaccaaa actcatcact acagacatac acaa                    2084
```

<210> SEQ ID NO 16
<211> LENGTH: 4329
<212> TYPE: DNA
<213> ORGANISM: Brassica rapa

<400> SEQUENCE: 16

```
ctcgaggcag tcactaacat gaagtttgac gaggagccca actatgggaa gcttatttct     60
cttttcgata tctcaattga gccgtgcgct ctatctagac caattagaat tgatggagct    120
ctaaaggttg ctggctgttt tcttgttcat atgattaact tctaaacttg tgtataaata    180
ttctctgaaa gtgcttcttt tggcatatgt aggttgggca aaaacgagga agattgcttc    240
tcaatttgga agaggatgaa cagccgaaga agaaaataag aataggcagt cctgctactc    300
aatggatctc agtctataac ggtcgtcgtc ccatgaaaca gaggtaaaac attttttgca    360
tatacacttt gaaagttcct cactaactgt gtaatctttt ggtagatatc actacaatgt    420
cggagagaca aggctgcgcc agcatataca aaagggaaat gaagatggcc ttttgattag    480
ctgtgtagca tcagcagcta atctctgggc tctcatcatg gatgctggaa ctggattcac    540
ttctcaagtt tatgagttgt caccggtctt cctacacaag gtaataatca gttgaagcaa    600
ttaagaatca atttgatttg tagtaaacta agaagaactt accttatgtt ttccccgcag    660
```

```
gactggatta tggaacaatg ggaaaagaac tactatataa gctccatagc tggttcagat    720
aacgggagct ctttagttgt tatgtcaaaa ggttagtgtt tagtgaataa taaacttata    780
ccacaaagtc ttcattgact tatttatata cttgttgtga attgctagga actacttatt    840
ctcagcagtc atacaaagtg agtgactcat ttccgttcaa gtggataaat aagaaatgga    900
aagaagattt tcatgtaacc tccatgacaa ctgctggtaa tcgttggggt gtggtaatgt    960
cgaggaactc tggcttctct gatcaggtag gttttttgtct cttattgtct ggtgttttta   1020 tttccctg atagtctaat atgataaact ctgcgttgtg aaaggtggtg gagcttgact       1080
ttttgtaccc aagcgatggg atacatagga ggtgggagaa tgggtataga ataacatcaa    1140
tggcagcaac tgcggatcaa gcagctttca tattaagcat accaaagcgt aagatggtgg    1200
atgaaactca agagactctc cgcaccaccg cctttccaag tactcatgtc aaggttggtt    1260
tctttagctt tgaacacaga tttggatctt tttgttttgt ttccatatac ttaggacctg    1320
agagcttttg gttgatttt ttttcaggac aaatgggcga agaatctgta cattgcatca     1380
atatgctatg gcaggacagt gtgctgatac acacttaagc atcatgtgga aagccaaaga    1440
caattggagc gagactcagg gtcgtcataa taccaatcaa agacgtaaaa ccagacgcaa    1500 cctcttttggt tgaatgtaat gaaagggatg tgtcttggta tgtatgtacg aataacaaaa   1560
gagaagatgg aattagtagt agaaatattt gggagctttt taagcccttc aagtgtgctt    1620
tttatcttat tgatatcatc catttgcgtt gtttaatgcg tctctagata tgttcctata    1680
tctttctcag tgtctgataa gtgaaatgtg agaaaaccat accaaaccaa aatattcaaa    1740
tcttattttt aataatgttg aatcactcgg agttgccacc ttctgtgcca attgtgctga    1800
atctatcaca ctagaaaaaa acatttcttc aaggtaatga cttgtggact atgttctgaa    1860
ttctcattaa gttttatttt tctgaagttt aagttttac cttctgttt gaaatatatc      1920 gttcataaga tgtcacgcca ggacatgagc tacacatcgc acatagcatg cagatcagga    1980
cgatttgtca ctcacttcaa acacctaaga gcttctctct cacagcgcac acacatatgc    2040
atgcaatatt tacacgtgat cgccatgcaa atctccattc tcacctataa attagagcct    2100
cggcttcact ctttactcaa accaaaactc atcactacag aacatacaca aatggcgaac    2160
aagctcttcc tcgtctcggc aactctcgcc ttgttcttcc ttctcaccaa tgcctccgtc    2220
tacaggacgg ttgtggaagt cgacgaagat gatgccacaa atccagccgg cccatttagg    2280
attccaaaat gtaggaagga gtttcagcaa gcacaacacc tgaaagcttg ccaacaatgg    2340
ctccacaagc aggcaatgca gtccggtagt ggtccaagct ggaccctcga tggtgagttt    2400
gattttgaag acgacgtgga gaaccaacaa cagggcccgc agcagaggcc accgctgctc    2460
cagcagtgct gcaacgagct ccaccaggaa gagccacttt gcgtttgccc aaccttgaaa    2520
ggagcatcca aagccgttaa acaacagatt cgacaacaac agggacaaca aatgcaggga    2580
cagcagatgc agcaagtgat tagccgtatc taccagaccg ctacgcactt acctagagct    2640
tgcaacatca ggcaagttag catttgcccc ttccagaaga ccatgcctgg gcccggcttc    2700
tactagattc caaacgaata tcctcgagag tgtgtatacc acggtgatat gagtgtggtt    2760
gttgatgtat gttaacacta catagtcatg gtgtgtgttc cataaataat gtactaatgt    2820
aataagaact actccgtaga cggtaataaa agagaagttt ttttttttac tcttgctact    2880
ttcctataaa gtgatgatta acaacagata caccaaaaag aaaacaatta atctatattc    2940
acaatgaagc agtactagtc tattgaacat gtcagatttt cttttttctaa atgtctaatt    3000 aagccttcaa ggctagtgat gataaaagat catccaatgg gatccaacaa agactcaaat    3060
```

```
ctggttttga tcagatactt caaaactatt tttgtattca ttaaattatg caagtgttct    3120
tttatttggt gaagactctt tagaagcaaa gaacgacaag cagtaataaa aaaaacaaag    3180
ttcagtttta agatttgtta ttgacttatt gtcatttgaa aaatatagta tgatattaat    3240
atagttttat ttatataatg cttgtctatt caagatttga gaacattaat atgatactgt    3300
ccacatatcc aatatattaa gtttcatttc tgttcaaaca tatgataaga tggtcaaatg    3360
attatgagtt ttgttattta cctgaagaaa agataagtga gcttcgagtt tctgaagggt    3420
acgtgatctt catttcttgg ctaaaagcga atatgacatc acctagagaa agccgataat    3480
agtaaactct gttcttggtt tttggtttaa tcaaaccgaa ccggtagctg agtgtcaagt    3540
cagcaaacat cgcaaaccat atgtcaattc gttagattcc cggtttaagt tgtaaaccgg    3600
tatttcattt ggtgaaaacc ctagaagcca gccacccttt ttaatctaat ttttgtaaac    3660
gagaagtcac cacacctctc cactaaaacc ctgaaccttta ctgagagaag cagagcgcag    3720
ctcaaagaac aaataaaacc cgaagatgag accaccacgt ggcggcggga gcttcagggg    3780
acggggagga agagatggcg gcggacgctt tggtggcggc ggcggacgtt tggtggcgg    3840 cggtggacgt tttggtggcg gcggtggacg ctttggtggt ggatatcgtg acgaaggacc    3900
tcccagtgaa gtcattggtt cgtttactct tttcttagtc gaatcttatt cttgctctgc    3960
tcgttgtttt accgataaag cttaagactt tattgataaa gttctcagct ttgaatgtga    4020
atgaactgtt tcctgcttat tagtgttcct ttgttttgag ttgaatcact gtcttagcac    4080
ttttgttaga ttcatctttg tgtttaagtt aaaaggtaga aactttgtga cttgtctccg    4140
ttatgacaag gttaactttg ttggttataa cagaagttgc gacctttctc catgcttgtg    4200
agggtgatgc tgtgaccaag ctctctcagg cgaagatccc ttacttcaat gccccaatct    4260
acttggaaaa caagacacag attgggaaag ttgatgagat ccaagcttgg gctgcaggtc    4320
gacgaattc                                                            4329

<210> SEQ ID NO 17
<211> LENGTH: 4274
<212> TYPE: DNA
<213> ORGANISM: Arabidopsis thaliana

<400> SEQUENCE: 17
ttttctttga tatttatttt attttttcca tggatagaga gagctaggca ttccggttat      60
ttggagattt tggaatttca attttgcggt ttggtatttt attttatttt atcaatttga     120
acgaaacaga gctttgtttt ggttacgatg cggtggattt tggttcggtt tagagtgata     180
tatatttggt accaaattaa accaagattc gttttcggta aaaacaaaat ttgattttta     240 agcattttg gaaaaattag tgttatatat atgagatttc ttaatcaaaa tctcactttt     300
atccgattta gtggtagttc ataaagtggt ttcatgtata tgatacctga ataaccaaca     360
tatgtatttt aagagacact tggaataata attctaaata tcctaactac tcgtgtccgt     420
atgttttgtc acggtgaaac gtgagaggac tagttttgt cacccgtcca taacattctt     480
agacatacat tactttggga gtgaaaaaca ttaagcttat cttatccat atattgtctt     540 accatcaata gacaatatcc aatggaccgg tgacctgcgt gtataagtaa ttttcaaga     600 tgctaaaact tttatgtatt tcagaattaa cctccaaaaa catttattga cacactacta     660 ctcttttccgt attgactctc aactagtcat ttcaaaataa ttgacatgtc agaacatgag     720
ttacacatgg ttgcatattg caagtagacg cggaaacttg tcacttcctt tacatttgag     780
```

```
tttccaacac ctaatcacga caacaatcat atagctctcg catacaaaca aacatatgca    840
tgtattctta cacgtgaact ccatgcaagt ctcttttctc acctataaat accaaccaca    900
ccttcaccac attcttcact cgaaccaaaa catacacaca tagcaaaaaa tggcaaacaa    960
gttgttcctc gtctgcgcag ctctcgctct ctgcttcctc ctcaccaacg cttccatcta   1020
ccgcaccgtc gttgagttcg aagaagatga cgccactaac cccataggcc caaaaatgag   1080
gaaatgccgc aaggagtttc agaaagaaca cacctaagag cttgccagc aattgatgct    1140 ccagcaagca aggcaaggcc gtagcgatga gtttgatttc gaagacgaca tggagaaccc   1200
acagggacaa cagcaggaac aacagctatt ccagcagtgc tgcaacgagc ttcgccagga   1260
agagccagat tgtgtttgcc ccaccttgaa acaagctgcc aaggccgtta gactccaggg   1320
acagcaccaa ccaatgcaag tcaggaaaat ttaccagaca gccaagcact tgcccaacgt   1380
ttgcgacatc ccgcaagttg atgtttgtcc cttcaacatc ccttcattcc cttctttcta   1440
ctaaatctca aacaaaccct caaagcgtat gagagtgtgg ttgttgatat atacatgttg   1500
acacttgaca cataccacac ctcatcgtgt gttttatgat aaatgtaagc ttttggatgt   1560
ttgagggtaa tgtaagcact acttaataaa taagagtttt gtttatattt tttttgtttg   1620
ttacattgct gctctctaaa aagtcatgac gcttacataa aaataacttt actccagtga   1680
actggaaaaa ttatagagta ccgctccacc tccacggaaa gatcatagac tagtactacc   1740
cagagatata aatcgtaatt aagacttcaa atgcgtagag acaaatggaa ttatgacttg   1800
gcaatttgat ctttcttgat atttttaaca aatggtttac gtatgtcttt atcaaacaaa   1860
aaaaagtaat aaatgtgttt aattattgag ttgtggctaa tagcacaatt ttaaaaaact   1920
gatgtccaat ttttctttt aaaaaaagct ataacgaagc atgtaaaaat gaacacttaa    1980
aaaataaaag tttcatttac gaatcatgta caattgtgga tttgagatta agaatccatc   2040
tgagaatagt ataccatttg tgatttgttt atgaatggta tgacaccata acgactata    2100 ctacagtttg agattcactg atcactcata gattttgaa taattcattt gaaaatgatt    2160
tgagattttt tttttaagtg aaatttagt tattttgaat tgttttttt tcttgtaaaa     2220 ggggtataat ccatattgaa attcgaccga tactcagtcg atagcctctt caccgaattt   2280
gctaatggac cttagccaag ccggagttaa aaaaatttac cggataaaaa ttgaaccaaa   2340
gagagaacaa actgagacaa tgcccgaaat atattactag acattcgcac cgcatgttac   2400
aaattaaacg gacatcgaaa actactacat acatactcaa ccttttttat aaactttat   2460 agccattttt tgccaattta tctataacgt aatactatgc attccctcat ttacatattt   2520
tttaacattg ttcgaagggt tgtgtgcccc gtgttaatat agagtcattt tctaacatct   2580
acaattcaga ttaagctccc aaacatatgt tccaattgca atataccacc aaattaaaag   2640
attgactctc acataccccca ttaattgaaa ccaaatgaac aaaaacgttc ataagatatt   2700
aagatgtcac gtcagaacat gatctacaaa tgacacataa catgcagacg cggagacgcg   2760
gagggccggt gttgttcgtc acttgtcact ctcttccaac acctaatcca gacaacaacc   2820
taagatcttc actctcgcac acacacgaca catgcattct tacacgtgat cgccatgcaa   2880
tctcctttct cacctataaa actaactctt cacttcactc tttactcaaa ccaaaactca   2940
tcatcacaaa cgagtaagaa tacaaacaca aatagcaaaa aaatggcaaa caagctcttc   3000
ctcgtctgcg caactttcgc cctctgcttc ctcctcacca acgcttccat ctaccgcact   3060
gttgtcgagt tcgacgaaga tgacgccagc aaccccatgg gccaagaca gaaatgtcag    3120 aaggagtttc agcaatcaca gcacctaaga gcttgccaga aattgatgcg catgcaaatg   3180
```

```
aggcaaggcc gtggtggtgg tccctccctc gacgatgagt tcgatttgga agacgacatc    3240
gagaacccac aaggccccca gcagggacac cagatcctcc agcagtgctg cagcgagctt    3300
cgccaggaag agccagtttg tgtttgcccc accttgagac aagctgccag ggccgttagc    3360
ctccagggac aacacggacc attccaatcc aggaaaattt acaagacagc taagtacttg    3420
cctaacattt gcaagatcca gcaagttggt gaatgcccct tccagaccac catcccttc    3480 ttccctcctt actaatagat tccaaacaaa aaccctcgag cgtatgagag tgtggttgtt    3540
gatacatgtt aacaccacac ctcatcgtgt cttttatgaa aatgtaagtt ttggatgttt    3600
gaggctaaat gtatttagca caagtcctta ataaataaga gttttgttta tgtttcattt    3660
tcattggcat atgctctctc taggttgtcc gtaatattag tttacaagaa aatctcccaa    3720
ataaatttac aggttaagca aattagcaat taaaaactgc tctatgactg tcctcctcta    3780
acaaatcaat tatattttc tcacaaccga agacatggtg aagataaatt tgcgagtcta    3840
acagacggtg tgttttcatt caagatgata gatttgcaac tagttctata tcatctgatc    3900
aactatcaag tattaaacat ttatccatat gatataatca aggaacacaa caccatggat    3960
aaaacacaaa accaaagcac agatccaatt agtgacccaa cacgaagaaa atttattcgc    4020
tatgagaatg aagcattatg catgtgtgaa tttacgccat agtctagtta ccaccgcccc    4080
accgcatgcg tgttaatatc tatttttggg gctcaagaaa ttgcacggca tcaagtggaa    4140
gagacatgcc aaattttaat tttaaattag atgatccatt ggaagcgaag ttcaaaaacg    4200
aaattttaca ttcatgatc ggtttgatcg atagtcgctt acaattgtgg taaaaaagtg    4260
ctagccattt tggc                                                     4274

<210> SEQ ID NO 18
<211> LENGTH: 1238
<212> TYPE: DNA
<213> ORGANISM: Arabidopsis thaliana

<400> SEQUENCE: 18
actagtcaac aattggccaa tctttgttct aaattgctaa taaacgacca tttccgtcaa      60
ttctccttgg ttgcaacagt ctacccgtca aatgtttact aatttataag tgtgaagttt     120
gaattatgaa agacgaaatc gtattaaaaa ttcacaagaa taaacaactc catagatttt     180
caaaaaaaca gtcacgagaa aaaaaccaca gtccgtttgt ctgctcttct agttttttatt   240 atttttctat taatagtttt ttgttatttc gagaataaaa tttgaacgat gtccgaacca     300
caaaagccga gccgataaat cctaagccga gcctaacttt agccgtaacc atcagtcacg     360
gctcccgggc taattcattt gaaccgaatc ataatcaacg gtttagatca aactcaaaac     420
aatctaacgg caacatagac gcgtcggtga gctaaaaaga gtgtgaaagc caggtcacca     480
tagcattgtc tctcccagat ttttatttg ggaaataata gaagaaatag aaaaaaataa     540
aagagtgaga aaaatcgtag agctatatat tcgcacatgt actcgtttcg ctttccttag     600
tgttagctgc tgccgctgtt gtttctcctc catttctcta tcttttctctc tcgctgcttc    660 tcgaatcttc tgtatcatct tcttcttctt caaggtgagt ctctagatcc gttcgcttga    720
ttttgctgct cgttagtcgt tattgttgat tctctatgcc gatttcgcta gatctgttta    780
gcatgcgttg tggttttatg agaaaatctt tgttttgggg gttgcttgtt atgtgattcg    840
atccgtgctt gttggatcga tctgagctaa ttccttaaggt ttatgtgtta gatctatgga   900
gtttgaggat tcttctcgct tctgtcgatc tctcgctgtt attttgtttt ttttcagtga    960
```

```
agtgaagttg tttagttcga aatgacttcg tgtatgctcg attgatctgg tttttaatctt    1020 cgatctgtta ggtgttgatg tttacaagtg aattctagtg ttttctcgtt gagatctgtg    1080
aagtttgaac ctagttttct caataatcaa catatgaagc gatgtttgag tttcaataaa    1140
cgctgctaat cttcgaaact aagttgtgat ctgattcgtg tttacttcat gagcttatcc    1200
aattcatttc ggtttcattt tactttttt ttagtgaa                              1238

<210> SEQ ID NO 19
<211> LENGTH: 110
<212> TYPE: DNA
<213> ORGANISM: Brassica rapa

<400> SEQUENCE: 19
aggacgattt gtcactcact tcaaacacct aagagcttct ctctcacagc gcacacacat      60
atgcatgcaa tatttacacg tgatcgccat gcaaatctcc attctcacct                110

<210> SEQ ID NO 20
<211> LENGTH: 120
<212> TYPE: DNA
<213> ORGANISM: Brassica juncea

<400> SEQUENCE: 20
ttcgccactt gtcactccct tcaaacacct aagagcttct ctctcacacg acacacatac      60
aatcacatgc gtgcatgcat tattacacgt gatcgccatg caaatctcct ttatagccta    120

<210> SEQ ID NO 21
<211> LENGTH: 105
<212> TYPE: DNA
<213> ORGANISM: Brassica napus

<400> SEQUENCE: 21
agaagaccat gcctgggccc tcctactaga ttccaaacga aaccctcgag tgtatgaatg      60
tggttgtcga tatatgtcaa caccacacct catcgcgtgt ttcat                    105

<210> SEQ ID NO 22
<211> LENGTH: 119
<212> TYPE: DNA
<213> ORGANISM: Brassica napus

<400> SEQUENCE: 22
tcgccacttg tcactccctt caaacaccta agagcttctc tctcacagca cacacataca      60
atcacatgcg tgcatgcatt attacacgtg atcgccatgc aaatctcctt tatagccta    119

<210> SEQ ID NO 23
<211> LENGTH: 119
<212> TYPE: DNA
<213> ORGANISM: Brassica oleracea

<400> SEQUENCE: 23
tcgccacttg tccctcccett caaacaccta agagcttctt taaaacagcc cacacagcca      60
atcacatgcg tgcatgcatt attacacgtg atcgccatgc aaatctccct tatcgccta    119

<210> SEQ ID NO 24
<211> LENGTH: 129
<212> TYPE: DNA
<213> ORGANISM: Brassica napus

<400> SEQUENCE: 24
agaagaccat gcctgggccc ggcttctact agattccaaa cgaaatatcc tcgagagtgt      60
```

```
gtataccacg gtgatatgag tgtggttgtt gatgtatgtt aacactacat agtcatggtg    120
tgtgttcca                                                            129

<210> SEQ ID NO 25
<211> LENGTH: 108
<212> TYPE: DNA
<213> ORGANISM: Brassica rapa

<400> SEQUENCE: 25
aggacgattt gtcactcact tcaaacacct aagagcttct ctctcacagc gcacacacat    60
atgcatgcaa tattacacgt gatgcatgca aatctccatt cttcacct                 108

<210> SEQ ID NO 26
<211> LENGTH: 115
<212> TYPE: DNA
<213> ORGANISM: Arabidopsis thaliana

<400> SEQUENCE: 26
agaccaccat ccctttcttc cctccttact aatagattcc aaacaaaaac cctcgagcgt    60
atgagagtgt ggttgttgat acatgttaac accacacctc atcgtgtctt ttatg        115

<210> SEQ ID NO 27
<211> LENGTH: 104
<212> TYPE: DNA
<213> ORGANISM: Brassica rapa

<400> SEQUENCE: 27
ttttattttc tgaagtttaa gttttttacct tctgttttga aatatatcgt tcataagatg   60
tcacgccagg acatgagcta cacatcgcac atagcatgca gatc                     104

<210> SEQ ID NO 28
<211> LENGTH: 120
<212> TYPE: DNA
<213> ORGANISM: Brassica juncea

<400> SEQUENCE: 28
tttttaattt tatgaagtta agttttttacc ttgttttttaa aaagaatcgt tcataagatg  60
ccatgccaga acattagcta cacgttacac atagcatgca gccgcggaga attgtttttc   120

<210> SEQ ID NO 29
<211> LENGTH: 120
<212> TYPE: DNA
<213> ORGANISM: Brassica napus

<400> SEQUENCE: 29
tttttaattt tatgaagtta agttttttacc ttgttttttaa aaagaatcgt tcataagatg  60
ccacgccaga acattagcta catgttacac atagcatgca gccgcggaga attgtttttc   120

<210> SEQ ID NO 30
<211> LENGTH: 120
<212> TYPE: DNA
<213> ORGANISM: Brassica napus

<400> SEQUENCE: 30
ttggtaattt tatgaagtta agttttttacc ttgttttttaa aaagaatcgt tcataagatg  60
ccatgccaga acattagcta cacgttacac atagcatgca gccgcggaga attgtttttc   120

<210> SEQ ID NO 31
```

-continued

```
<211> LENGTH: 120
<212> TYPE: DNA
<213> ORGANISM: Brassica napus

<400> SEQUENCE: 31
caacaaattc agcaacaggg acaacagcaa ggaaagctgc aaatggtgag ccgtatctac      60
cagacagcta ctcacttacc taaagtttgc aaaatcccgc aagttagcgt atgtcccttc     120

<210> SEQ ID NO 32
<211> LENGTH: 121
<212> TYPE: DNA
<213> ORGANISM: Brassica oleracea

<400> SEQUENCE: 32
ttggtaattt tttgaagttg agttttacc ttgttttgga agggagtcgt tcatgagatg       60
ccatgccaga acattagcta gccggttaca catagcatgc agccgcggag gattgttttt     120
c                                                                     121

<210> SEQ ID NO 33
<211> LENGTH: 133
<212> TYPE: DNA
<213> ORGANISM: Brassica napus

<400> SEQUENCE: 33
caacaggttc gacaacaaca gggacaacaa atgcagggac agcagatgca gcaagtaatt      60
agccgtgtct accagactgc tacgcactta cctagagttt gcaacatcag gcaagttagc     120
atttgtccct tcc                                                        133

<210> SEQ ID NO 34
<211> LENGTH: 129
<212> TYPE: DNA
<213> ORGANISM: Brassica rapa

<400> SEQUENCE: 34
ttttattttc gcgaagttaa gttttacct tctgtttga aatatatcgt tcataacatc        60
gttctcacgc caggaccatt gcagctacat accattgcag catctaccat tcgccatgca     120
atgcagatc                                                             129

<210> SEQ ID NO 35
<211> LENGTH: 103
<212> TYPE: DNA
<213> ORGANISM: Arabidopsis thaliana

<400> SEQUENCE: 35
ctccagggac aacacggacc attccaatcc aggaaaattt acaagacagc taagtacttg      60
cctaacattt gcaagatcca gcaagttggt gaatgcccct tcc                       103

<210> SEQ ID NO 36
<211> LENGTH: 1348
<212> TYPE: DNA
<213> ORGANISM: Artificial Sequence
<220> FEATURE:
<223> OTHER INFORMATION: Chimeric promoter sequence using enhancer from
      Brassica rapa

<400> SEQUENCE: 36
actagtcaac aattggccaa tctttgttct aaattgctaa taaacgacca tttccgtcaa      60
ttctccttgg ttgcaacagt ctacccgtca aatgtttact aatttataag tgtgaagttt     120
```

```
gaattatgaa agacgaaatc gtattaaaaa ttcacaagaa taaacaactc catagatttt      180
caaaaaaaca gtcacgagaa aaaaccaca gtccgtttgt ctgctcttct agttttatt      240 attttctat taatagtttt ttgttatttc gagaataaaa tttgaacgat gtccgaacca      300
caaaagccga gccgataaat cctaagccga gcctaacttt agccgtaacc atcagtcacg      360
gctcccgggc taattcattt gaaccgaatc ataatcaacg gtttagatca aactcaaaac      420
aatctaacgg caacatagac gcgtcggtga gctaaaaaga gtgtgaaagc caggtcacca      480
tagcattgtc tctcccagat tttttatttg ggaaataata gaagaaatag aaaaaaataa      540
aagagtgaga aaaatcgtag agctatatat tcgcacatgt actcgtttcg ctttccttag      600
aggacgattt gtcactcact tcaaacacct aagagcttct ctctcacagc gcacacacat      660
atgcatgcaa tatttacacg tgatcgccat gcaaatctcc attctcacct tgttagctgc      720
tgccgctgtt gtttctcctc catttctcta tctttctctc tcgctgcttc tcgaatcttc      780
tgtatcatct tcttcttctt caaggtgagt ctctagatcc gttcgcttga ttttgctgct      840
cgttagtcgt tattgttgat tctctatgcc gatttcgcta gatctgttta gcatgcgttg      900
tggttttatg agaaaatctt tgttttgggg gttgcttgtt atgtgattcg atccgtgctt      960
gttggatcga tctgagctaa ttcttaaggt ttatgtgtta gatctatgga gtttgaggat     1020
tcttctcgct tctgtcgatc tctcgctgtt attttttgttt ttttcagtga agtgaagttg     1080
tttagttcga aatgacttcg tgtatgctcg attgatctgg ttttaatctt cgatctgtta     1140
ggtgttgatg tttacaagtg aattctagtg ttttctcgtt gagatctgtg aagtttgaac     1200
ctagttttct caataatcaa catatgaagc gatgtttgag tttcaataaa cgctgctaat     1260
cttcgaaact aagttgtgat ctgattcgtg tttacttcat gagcttatcc aattcatttc     1320
ggtttcattt tactttttttt ttagtgaa                                       1348
```

<210> SEQ ID NO 37
<211> LENGTH: 1342
<212> TYPE: DNA
<213> ORGANISM: Artificial Sequence
<220> FEATURE:
<223> OTHER INFORMATION: Chimeric promoter sequence using enhancer from
      Brassica rapa

<400> SEQUENCE: 37

```
actagtcaac aattggccaa tctttgttct aaattgctaa taaacgacca tttccgtcaa       60
ttctccttgg ttgcaacagt ctacccgtca aatgtttact aatttataag tgtgaagttt      120
gaattatgaa agacgaaatc gtattaaaaa ttcacaagaa taaacaactc catagatttt      180
caaaaaaaca gtcacgagaa aaaaccaca gtccgtttgt ctgctcttct agttttatt      240 attttctat taatagtttt ttgttatttc gagaataaaa tttgaacgat gtccgaacca      300
caaaagccga gccgataaat cctaagccga gcctaacttt agccgtaacc atcagtcacg      360
gctcccgggc taattcattt gaaccgaatc ataatcaacg gtttagatca aactcaaaac      420
aatctaacgg caacatagac gcgtcggtga gctaaaaaga gtgtgaaagc caggtcacca      480
tagcattgtc tctcccagat tttttatttg ggaaataata gaagaaatag aaaaaaataa      540
aagagtgaga aaaatcgtag agctatatat tcgcacatgt actcgtttcg ctttccttag      600 ttttatttc tgaagtttaa gttttacct tctgttttga aatatatcgt tcataagatg      660
tcacgccagg acatgagcta cacatcgcac atagcatgca gatctgttag ctgctgccgc      720
tgttgtttct cctccatttc tctatctttc tctctcgctg cttctcgaat cttctgtatc      780
```

-continued

```
atcttcttct tcttcaaggt gagtctctag atccgttcgc ttgattttgc tgctcgttag      840
tcgttattgt tgattctcta tgccgatttc gctagatctg tttagcatgc gttgtggttt      900
tatgagaaaa tctttgtttt gggggttgct tgttatgtga ttcgatccgt gcttgttgga      960
tcgatctgag ctaattctta aggtttatgt gttagatcta tggagtttga ggattcttct     1020
cgcttctgtc gatctctcgc tgttattttt gtttttttca gtgaagtgaa gttgtttagt     1080
tcgaaatgac ttcgtgtatg ctcgattgat ctggttttaa tcttcgatct gttaggtgtt     1140
gatgtttaca agtgaattct agtgttttct cgttgagatc tgtgaagttt gaacctagtt     1200
ttctcaataa tcaacatatg aagcgatgtt tgagtttcaa taaacgctgc taatcttcga     1260
aactaagttg tgatctgatt cgtgtttact tcatgagctt atccaattca tttcggtttc     1320 attttactttt tttttttagtg aa                                             1342
```

1
CHIMERIC PROMOTERS AND THEIR USES THEREOF IN PLANTS

This application claims the benefit of U.S. Provisional Patent Application No. 61/037,126 filed Mar. 17, 2008, herein incorporated by reference in its entirety.

INCORPORATION OF SEQUENCE LISTING

The sequence listing that is contained in the file named "MONS223WO_seq_ST25.txt", which is 47 kilobytes (as measured in Microsoft Windows®) and was created on Mar. 11, 2009, is filed herewith by electronic submission and is incorporated by reference herein.

BACKGROUND OF THE INVENTION

1. Field of the Invention

The invention relates to the field of plant molecular biology and plant genetic engineering and DNA molecules useful for modulating gene expression in plants.

2. Description of Related Art

Promoters are genetic elements that regulate gene activity by modulating the transcription of an operably linked transcribable polynucleotide molecule. Promoters may be defined as constitutive, i.e. generally always active, or by their temporal, spatial, developmental, tissue, environmental, physiological, pathological, cell cycle, and/or chemically responsive expression pattern, and any combination thereof, as well as by quantitative or qualitative indications.

SUMMARY OF THE INVENTION

The present invention provides novel chimeric promoters and enhancers for use in plants. The present invention also provides DNA constructs comprising the chimeric promoters. The present invention also provides transgenic plant cells, plants, and seeds comprising the chimeric promoters operably linked to a transcribable polynucleotide molecule. The present invention also provides methods of making and using the chimeric promoters, the DNA constructs comprising the chimeric promoters, and the transgenic plant cells, plants, and seeds comprising the chimeric promoters operably linked to a transcribable polynucleotide molecule.

BRIEF DESCRIPTION OF THE SEQUENCE LISTING

Figure 1:
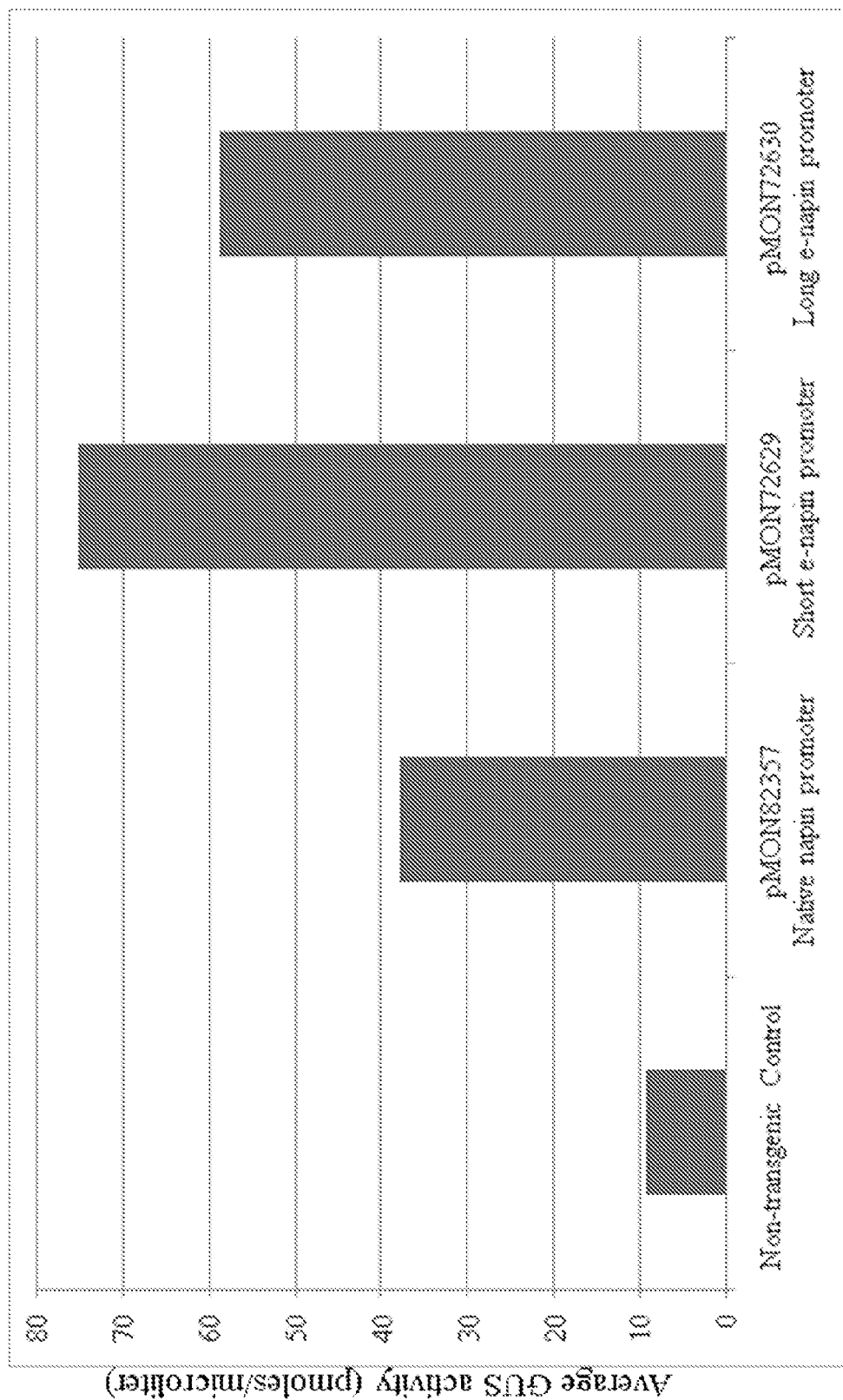
FIG. 1 illustrates the average GUS activity in picomoles/microliter measured in seed from canola plants transformed with a construct in which the native napin promoter, short e-napin promoter, or long e-napin promoter was operably linked to the *E. coli* beta-glucuronidase gene. Data from non-transgenic canola plants is also provided as a control.

SEQ ID NO: 1 is the DNA sequence of the short e-napin chimeric promoter.

SEQ ID NO: 2 is the DNA sequence of the long e-napin chimeric promoter.

SEQ ID NO: 3 is the DNA sequence of the short e-napin chimeric promoter plus napin leader.

SEQ ID NO: 4 is the DNA sequence of the long e-napin chimeric promoter plus napin leader.

SEQ ID NO: 5 is the DNA sequence of the napin leader.

SEQ ID NO: 6 is the DNA sequence of a native napin promoter plus napin leader from *Brassica rapa* (cv. 'Ebony').

SEQ ID NO: 7 is the DNA sequence of a native napin promoter from *Brassica rapa* (cv. 'Ebony').

SEQ ID NO: 8 is the DNA sequence of a native napin promoter from *Brassica juncea*.

SEQ ID NO: 9 is the DNA sequence of a native napin promoter from *Brassica napus* (rape).

SEQ ID NO: 10 is the DNA sequence of a native napin promoter from *Brassica napus* (rape).

SEQ ID NO: 11 is the DNA sequence of a native napin promoter from *Brassica napus* (rape).

SEQ ID NO: 12 is the DNA sequence of a native napin promoter from *Brassica napus* (rape).

SEQ ID NO: 13 is the DNA sequence of a native napin promoter from *Brassica oleracea*.

SEQ ID NO: 14 is the DNA sequence of a native napin promoter from *Brassica napus* (rape).

SEQ ID NO: 15 is the DNA sequence of a native napin promoter from *Brassica rapa*.

SEQ ID NO: 16 is the DNA sequence of a native napin promoter from *Brassica rapa*.

SEQ ID NO: 17 is the DNA sequence of a native napin promoter from *Arabidopsis thaliana*.

SEQ ID NO: 18 is the DNA sequence of a native actin 7 promoter from *Arabidopsis thaliana*.

SEQ ID NO: 19 is the DNA sequence of a highly conserved domain enhancer element.

SEQ ID NO: 20 is the DNA sequence of a highly conserved domain enhancer element.

SEQ ID NO: 21 is the DNA sequence of a highly conserved domain enhancer element.

SEQ ID NO: 22 is the DNA sequence of a highly conserved domain enhancer element.

SEQ ID NO: 23 is the DNA sequence of a highly conserved domain enhancer element.

SEQ ID NO: 24 is the DNA sequence of a highly conserved domain enhancer element.

SEQ ID NO: 25 is the DNA sequence of a highly conserved domain enhancer element.

SEQ ID NO: 26 is the DNA sequence of a highly conserved domain enhancer element.

SEQ ID NO: 27 is the DNA sequence of a conserved domain enhancer element.

SEQ ID NO: 28 is the DNA sequence of a conserved domain enhancer element.

SEQ ID NO: 29 is the DNA sequence of a conserved domain enhancer element.

SEQ ID NO: 30 is the DNA sequence of a conserved domain enhancer element.

SEQ ID NO: 31 is the DNA sequence of a conserved domain enhancer element.

SEQ ID NO: 32 is the DNA sequence of a conserved domain enhancer element.

SEQ ID NO: 33 is the DNA sequence of a conserved domain enhancer element.

SEQ ID NO: 34 is the DNA sequence of a conserved domain enhancer element.

SEQ ID NO: 35 is the DNA sequence of a conserved domain enhancer element.

SEQ ID NO: 36 is the DNA sequence of the short e-actin chimeric promoter.

SEQ ID NO: 37 is the DNA sequence of the long e-actin chimeric promoter.

DETAILED DESCRIPTION OF THE INVENTION

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e., a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein is that required by Title 37 of the United States Code of Federal Regulations §1.822 and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native or natural state. In one embodiment, the term "isolated" refers to a DNA molecule that is at least partially separated from the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated even when integrated into the chromosome of a host cell or present in a nucleic acid solution with other DNA molecules.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term "sequence identity" refers to the extent to which two optimally aligned polynucleotide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. Other methods useful for aligning sequences are well known to those skilled in the art, such as the computerized implementations of the alignment algorithms of Smith and Waterman (Smith and Waterman, *Advances in Applied Mathematics*, 2:482-489, 1981, Smith et al., *Nucleic Acids Research*, 11:2205-2220 (1983)) and Needleman and Wunsch (Needleman and Wunsch, *Journal of Molecular Biology*, 48:443-453 (1970)). Computer implementations of these are available from EMBOSS (Rice, P. Longden, I. and Bleasby, A., "EMBOSS: The European Molecular Biology Open Software Suite" *Trends in Genetics* 16:276-277 (2000)). As used herein, the term "reference sequence" refers to a sequence provided as SEQ ID NO: 1-4 and 19-35.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NO: 1-4 and 19-35, has at least 90 percent identity or higher, about 95 percent identity or higher, or at least 96 percent identity, 97 percent identity, 98 percent identity, or 99 percent identity to the reference sequence and has gene regulatory activity.

Promoters

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more DNA molecules. Promoters useful in practicing the present invention include SEQ ID NO: 1-4, 6-18, 36-37 or fragments or variants thereof.

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention. Chimeric promoters useful in practicing the present invention include SEQ ID NO: 1-4 and 36-37.

Promoters may be characterized by their expression pattern, i.e. as constitutive and/or by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. Expression may be characterized by its temporal, spatial, developmental, tissue, environmental, physiological, pathological, cell cycle, and/or chemically responsive qualities as well as by quantitative or qualitative indications. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression is any pattern of translation of a transcribed RNA molecule into a protein molecule. Protein expression may be characterized by its temporal, spatial, developmental, or morphological qualities as well as by quantitative or qualitative indications.

As used herein, the term "gene regulatory activity" refers to the ability to affect the expression pattern of an operably linked transcribable polynucleotide molecule by affecting the transcription and/or translation of that operably linked transcribable polynucleotide molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

As used herein, the term "regulatory element" refers to a DNA molecule having gene regulatory activity, i.e. one that has the ability to affect the transcription and/or translation of an operably linked transcribable polynucleotide molecule. Regulatory elements such as promoters, leaders, introns, and transcription termination regions are DNA molecules that have gene regulatory activity and play an integral part in the overall expression of genes in living cells. Isolated regulatory elements, such as promoters, that function in plants are therefore useful for modifying plant phenotypes through the methods of genetic engineering.

In one embodiment, fragments are provided of a promoter sequence disclosed herein. Promoter fragments may exhibit promoter activity, and may be useful alone or in combination with other promoters and promoter fragments, such as in constructing chimeric promoters. In specific embodiments, fragments of a promoter are provided comprising at least about 50, 95, 150, 250, 500, or about 750 contiguous nucleotides of a polynucleotide molecule having promoter activity disclosed herein.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. In the present invention, a polynucleotide sequence provided as SEQ ID NO: 1-4 may be used to create variants that are in composition similar, but not identical to, the polynucleotide sequence of the original promoter, while still maintaining the general functionality, i.e. same or similar expression pattern, of the original promoter. Production of such variants of the present invention is well within the ordinary skill of the art in light of the disclosure and is encompassed within the scope of the present invention.

A promoter or promoter fragment may also be analyzed for the presence of known promoter elements, i.e. DNA sequence characteristics, such as a TATA-box and other known transcription factor binding site motifs. Identification of such known promoter elements may be used by one of skill in the art to design variants of the promoter having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box. A promoter may naturally comprise one or more enhancer elements that affect the transcription of an operably linked polynucleotide sequence. An isolated enhancer element may also be fused to a promoter to produce a chimeric promoter. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e., operably linked. As used herein, the term "vector" means any recombinant polynucleotide construct that may be used for the purpose of transformation, i.e., the introduction of heterologous DNA into a host cell.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell.

The constructs of the present invention are generally double Ti plasmid border DNA constructs that have the right border (RB) and left border (LB) regions of the Ti plasmid isolated from *Agrobacterium tumefaciens* comprising a T-DNA, that along with transfer molecules provided by the *Agrobacterium tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404; however, other strains known to those skilled in the art of plant transformation can function in the present invention.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art, see, for example, *Molecular Cloning: A Laboratory Manual*, $3^{rd}$ edition Volumes 1, 2, and 3, J. F. Sambrook, D. W. Russell, and N. Irwin, Cold Spring Harbor Laboratory Press (2000). Methods for making recombinant vectors particularly suited to plant transformation include, without limitation, those described in U.S. Pat. Nos. 4,971,908; 4,940,835; 4,769,061; and 4,757,011. These types of vectors have also been reviewed in the scientific literature (see, for example, Rodriguez, et al., *Vectors: A Survey of Molecular Cloning Vectors and Their Uses*, Butterworths, Boston, (1988) and Glick, et al., *Methods in Plant Molecular Biology and Biotechnology*, CRC Press, Boca Raton, Fla. (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology*, 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA*, 82: 5824-5828 (1985)).

Various regulatory elements may be included in a construct. Any such regulatory elements may be provided in combination with other regulatory elements. Such combinations can be designed or modified to produce desirable regulatory features. Constructs of the present invention would typically comprise at least one regulatory element operably linked to a transcribable polynucleotide molecule operably linked to a 3' transcription termination molecule.

As used herein, the term "leader" refers to a DNA molecule isolated from the untranslated 5' region (5' UTR) of a genomic copy of a gene and defined generally as a segment between the transcription start site (TSS) and the coding sequence start site. Alternately, leaders may be synthetically produced or manipulated DNA elements. A leader can be used as a 5' regulatory element for modulating expression of an operably linked transcribable polynucleotide molecule. For example, non-translated 5' leaders derived from heat shock protein genes have been demonstrated to enhance gene expression in plants (see, for example, U.S. Pat. Nos. 5,659,122 and 5,362,865). Promoter molecules of the present invention may optionally comprise a native leader linked to the plant promoter segment for which it is naturally found. This molecule may be replaced with a heterologous leader.

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain elements enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347).

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et al., *Proc. Natl. Acad. Sci. USA*, 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. No. 5,188,642 and U.S. Pat. No. 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.*, 210:437-442 (1987)) or the *Petunia hybrida* EPSPS CTP (CTP4) (See, della-Cioppa et al., *Proc. Natl. Acad. Sci. USA*, 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those having sequences useful for gene suppression. A "transgene" refers to a transcribable polynucleotide molecule heterologous to a host cell and/or a transcribable polynucleotide molecule artificially incorporated into a host cell's genome.

A promoter of the present invention may be operably linked to a transcribable polynucleotide molecule that is heterologous with respect to the promoter molecule. As used herein, the term "heterologous" refers to the combination of two or more polynucleotide molecules when such a combination would not normally be found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of an RNA transcript is desired. Such expression of an RNA transcript may result in translation of the resulting mRNA molecule and thus protein expression. Alternatively, a transcribable polynucleotide molecule may be designed to ultimately cause decreased expression of a specific gene or protein. This may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a chimeric promoter of the present invention, such as those provided as SEQ ID NO: 1-4, operably linked to a transcribable polynucleotide molecule so as to modulate transcription of the transcribable polynucleotide molecule at a desired level or in a desired pattern upon introduction of said construct into a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type provides a desirable characteristic associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest known in the art include those for herbicide resistance (U.S. Pat. Nos. 6,803, 501; 6,448,476; 6,248,876; 6,225,114; 6,107,549; 5,866,775; 5,804,425; 5,633,435; and 5,463,175), increased yield (U.S. Pat. No. USRE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653, 280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013, 864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444, 876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822, 141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171, 640), biopolymers (U.S. Pat. Nos. USRE37,543; 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689, 041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding a RNA molecule that causes the targeted modulation of gene expression of an endogenous gene, for example via antisense (See, e.g., U.S. Pat. No. 5,107,065); inhibitory RNA ("RNAi", including modulation of gene expression via miRNA-, siRNA-, trans-acting siRNA-, and phased siRNA-mediated mechanisms, e.g., as described in published applications US 2006/0200878 and US 2008/0066206, and in U.S. patent application Ser. No. 11/974,469); or cosuppression-mediated mechanisms. The RNA could also be a catalytic RNA molecule (e.g., a ribozyme or a riboswitch; see e.g., US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US2007/0124836) and compositions isolated from nematode pests (U.S. Patent Publication No. US2007/0250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS described in U.S. Pat. No. 5,599,670), green fluorescent protein and variants thereof (GFP described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, dalapon, dicamba, cyclohexanedione, protoporphyrinogen oxidase inhibitors, and isoxaflutole herbicides. Transcribable polynucleotide molecules encoding proteins involved in herbicide tolerance are known in the art, and include, but are not limited to, a transcribable polynucleotide molecule encoding 5-enolpyruvylshikimate-3-phosphate synthase (EPSPS for glyphosate tolerance described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtI) described in Misawa, et al., *Plant Journal*, 4:833-840 (1993) and Misawa, et al., *Plant Journal*, 6:481-489 (1994) for norflurazon tolerance; a transcribable polynucleotide molecule encoding acetohydroxyacid synthase (AHAS, aka ALS) described in Sathasiivan, et al., *Nucl. Acids Res.*, 18:2188-2193 (1990) for tolerance to sulfonylurea herbicides; and the bar gene described in DeBlock, et al., *EMBO Journal*, 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.*, 42: 205 (1991)).

Technology for introduction of a DNA molecule into cells is well known to those of skill in the art. Methods and materials for transforming plant cells by introducing a plant DNA construct into a plant genome in the practice of this invention can include any of the well-known and demonstrated methods including, but not limited to:

(1) chemical methods (Graham and Van der Eb, *Virology*, 54(2):536-539 (1973) and Zatloukal, et al., *Ann. N.Y. Acad. Sci.*, 660: 136-153 (1992));

(2) physical methods such as microinjection (Capecchi, *Cell*, 22(2):479-488 (1980)), electroporation (Wong and Neumann, *Biochim. Biophys. Res. Commun.*, 107(2): 584-587 (1982); Fromm, et al, *Proc. Natl. Acad. Sci. USA*, 82(17):5824-5828 (1985); U.S. Pat. No. 5,384, 253) particle acceleration (Johnston and Tang, *Methods Cell Biol.*, 43(A):353-365 (1994); Fynan, et al., *Proc. Natl. Acad. Sci. USA*, 90(24):11478-11482 (1993)): and microprojectile bombardment (as illustrated in U.S. Pat. Nos. 5,015,580; 5,550,318; 5,538,880; 6,160,208; 6,399,861; and 6,403,865);

(3) viral vectors (Clapp, *Clin. Perinatol.*, 20(1):155-168 (1993); Lu, et al., *J. Exp. Med.*, 178(6):2089-2096 (1993); Eglitis and Anderson, *Biotechniques*, 6(7):608-614 (1988));

(4) receptor-mediated mechanisms (Curiel et al., *Hum. Gen. Ther.*, 3(2):147-154 (1992) and Wagner, et al., *Proc. Natl. Acad. Sci. USA*, 89(13):6099-6103 (1992);

(5) bacterial mediated mechanisms such as *Agrobacterium*-mediated transformation (as illustrated in U.S. Pat. Nos. 5,824,877; 5,591,616; 5,981,840; and 6,384,301);

(6) direct introduction into pollen by injecting a plant's reproductive organs (Zhou, et al., *Methods in Enzymology*, 101:433, (1983); Hess, *Intern Rev. Cytol.*, 107:367 (1987); Luo, et al., *Plant Mol. Biol. Reporter*, 6:165 (1988); Pena, et al., *Nature*, 325:274 (1987));

(7) protoplast transformation (as illustrated in U.S. Pat. No. 5,508,184); and (8) injection into immature embryos (Neuhaus, et al., *Theor. Appl. Genet.*, 75:30 (1987)).

Any of the above described methods may be utilized to transform a host cell with one or more promoters and/or constructs of the present. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Methods for transforming dicotyledonous plants, primarily by use of *Agrobacterium tumefaciens* and obtaining transgenic plants have been published for cotton (U.S. Pat. Nos. 5,004,863; 5,159,135; and 5,518,908); soybean (U.S. Pat. Nos. 5,569,834 and 5,416,011; see also, McCabe, et al., *Biotechnology*, 6:923 (1988) and Christou et al., *Plant Physiol.* 87:671-674 (1988)); *Brassica* (U.S. Pat. No. 5,463, 174); peanut (Cheng et al., *Plant Cell Rep.*, 15:653-657 (1996) and McKently et al., *Plant Cell Rep.*, 14:699-703 (1995)); papaya; and pea (Grant et al., *Plant Cell Rep.*, 15:254-258 (1995)).

Transformations of monocotyledon plants using electroporation, particle bombardment, and *Agrobacterium* have also been reported. Transformation and plant regeneration have been achieved in asparagus (Bytebier, et al., *Proc. Natl. Acad. Sci. (USA)*, 84:5354 (1987); barley (Wan and Lemaux, *Plant Physiol*, 104:37 (1994)); maize (Rhodes, et al., *Science* 240: 204 (1988), Gordon-Kamm, et al., *Plant Cell*, 2:603-618 (1990), Fromm, et al., *Bio/Technology*, 8:833 (1990), Koziel et al., *Bio/Technology*, 11:194 (1993), and Armstrong, et al., *Crop Science*, 35:550-557 (1995)); oat (Somers, et al., *Bio/Technology*, 10:1589 (1992)); orchard grass (Horn, et al., *Plant Cell Rep.* 7:469 (1988)); rye (De la Pena, et al., *Nature*, 325:274 (1987)); sugarcane (Bower and Birch, *Plant Journal*, 2:409 (1992)); tall fescue (Wang, et al., *Bio/Technology*, 10:691 (1992)); and wheat (Vasil, et al., *Bio/Technology*, 10:667 (1992) and U.S. Pat. No. 5,631,152).

The regeneration, development, and cultivation of plants from transformed plant protoplast or explants is well known in the art (see, for example, Weissbach and Weissbach, *Methods for Plant Molecular Biology*, (Eds.), Academic Press, Inc., San Diego, Calif. (1988) and Horsch et al., *Science*, 227:1229-1231 (1985)). Transformed cells are generally cultured in the presence of a selective media, which selects for the successfully transformed cells and induces the regeneration of plant shoots and roots into intact plants (Fraley, et al., *Proc. Natl. Acad. Sci. U.S.A.*, 80: 4803 (1983)). Transformed plants are typically obtained within two to four months.

The regenerated transgenic plants are self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, Calif., 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses*, 2nd Edition, Monograph., 16:249 (1987); Fehr, *Principles of variety development, Theory and Technique*, (Vol 1) and *Crop Species Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immuno-precipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Chimeric promoters useful to drive expression of an operably linked transcribable polynucleotide in transgenic plants were constructed, and the expression pattern of these promoters was analyzed in transgenic plants.

Example 1

Construction of Chimeric Promoters

Chimeric promoters are created by fusing at least one enhancer element isolated from a napin promoter of *Brassica* with a promoter. Enhancer elements isolated from a napin promoter of *Brassica* and useful in practicing the invention are provided as SEQ ID NO:19-35. The chimeric promoter is constructed with at least one enhancer element provided in SEQ ID NOs: 19-35, but may have two or more copies of any enhancer element or combination of enhancer elements provided in SEQ ID NOs:19-35. The enhancer element can be inserted as a DNA fragment at any location within the promoter molecule or fused at the 5' or 3' end of the promoter molecule. A chimeric promoter may optionally contain additional polynucleotides such as those having DNA sequences for restrictions endonuclease sites, recombination sites, or ligation-independent cloning sites. These additional polynucleotides may optionally be located between an enhancer element and the promoter.

Promoters useful in practicing the invention include any promoter capable of expressing an operably linked transcribable polynucleotide molecule in plants. An example of promoters useful in practicing the invention would be native napin promoters. A native napin promoter includes any promoter derived from the 5' end of a genomic copy of a napin gene. A napin gene is a gene encoding a napin protein. Napin proteins are a family of low-molecular weight basic seed storage proteins synthesized in the embryo during seed maturation. Examples of native napin promoters useful in practicing the invention are provided as SEQ ID NO:6-17. Further examples of promoters useful in practicing the invention would include any promoter derived from the 5' end of a genomic copy of an actin gene, such as the *Arabidopsis thaliana* Act7 promoter (SEQ ID NO:18) and other actin promoters known in the art, see for example U.S. Pat. No. 7,408,054 and PCT Publication No. WO 01/44457.

Two chimeric promoters, referred to herein as short e-napin (SEQ ID NO:1) and long e-napin (SEQ ID NO:2), were created by combining a native napin promoter with an enhancer element isolated from the native napin promoter. The short e-napin chimeric promoter (SEQ ID NO:1) was constructed by combining an enhancer element (SEQ ID NO:19) with a native napin promoter (SEQ ID NO:7). The short e-napin promoter plus leader (SEQ ID NO:3) is comprised of the short e-napin promoter (SEQ ID NO:1) and a napin leader (SEQ ID NO:5) contiguously arranged in the 5' to 3' direction. The long e-napin chimeric promoter (SEQ ID NO:2) was constructed by combining an enhancer element (SEQ ID NO:27) with a native napin promoter (SEQ ID NO:7). The long e-napin promoter plus leader (SEQ ID NO:4) is comprised of the long e-napin promoter (SEQ ID NO:2) and a napin leader (SEQ ID NO:5) contiguously arranged in the 5' to 3' direction. The native napin promoter plus leader (SEQ ID NO:6) is comprised of a native napin promoter (SEQ ID NO:7) and a short leader sequence (SEQ ID NO:5) contiguously arranged in the 5' to 3' direction.

A chimeric promoter comprising a native actin promoter may be created by combining a native actin promoter with at least one enhancer element provided as SEQ ID NO:19-35 using methods to manipulate DNA molecules well known in the art. For example, a single enhancer element provided as SEQ ID NO:19 may be inserted within the *A. thaliana* Actin 7 promoter (SEQ ID NO:18). Such insertion may be between the core promoter element and leader of the *A. thaliana* Actin 7 promoter. The resulting sequence, referred to herein as the short e-actin 7 promoter, is provided as SEQ ID NO:36. Likewise, a single enhancer element provided as SEQ ID NO:27 may be inserted within the *A. thaliana* Actin 7 promoter (SEQ ID NO:18) between the core promoter element and leader of the promoter. The resulting sequence, referred to herein as the long e-actin 7 promoter, is provided as SEQ ID NO:37. Other chimeric promoters comprising the *A. thaliana* Actin 7 promoter may be made by using one or more of the enhancer elements SEQ ID NO:19-35.

Chimeric promoters may be operably linked to a transcribable polynucleotide sequence in a plant transformation construct. The plant transformation construct can be used to produce transgenic plants or in a transient protoplast assay from protoplasts derived from plant tissue to analyze the expression pattern of the chimeric promoter.

Example 2

GUS Expression Analysis

Canola plants were transformed with plant transformation vectors containing the native napin promoter (pMON82357), the short e-napin promoter (pMON72629), and the long e-napin promoter (pMON72630), respectively, each driving the expression of an *E. coli* beta-glucuronidase gene (GUS, described in U.S. Pat. No. 5,599,670) to evaluate the synthetic enhanced promoters.

Canola plants (*Brassica napus*) were transformed using a modification of the protocol described by Radke et al., (*Plant Cell Reports* 11:499-505, 1992). Briefly, canola seed of the cultivar 'Ebony' (Monsanto Canada, Inc., Winnipeg, Canada) was disinfected and germinated in vitro as described in Radke et al., 1992. Pre-cocultivation with tobacco feeder plates, explant preparation, and inoculation of explants with *Agrobacterium tumefaciens* strain ABI (Koncz and Schell, *Mol Gen Genet.* 204:383-396 (1986)) containing the vector pMON72629, pMON72630, or pMON82357 was done as described with the *Agrobacterium* being maintained in LB media (solid or liquid) containing 75 mg/l spectinomycin, 25 mg/liter chloramphenicol and 50 mg/liter kanamycin. For plant transformation including callus induction, shoot regeneration, maturation, and rooting, glyphosate selection was used. Specifically, the B5-1 callus induction medium was supplemented with 500 mg/liter carbenicillin and 50 mg/liter Timentin (Duchefa Biochemie BV) to inhibit the *Agrobacterium* growth and kanamycin was omitted from the media. B5BZ shoot regeneration medium contained 500 mg/liter carbenicillin, 50 mg/liter, Timentin and 45 mg/liter glyphosate with explants being transferred to fresh medium every two weeks. Glyphosate-selected shoots were transferred to hormone-free B5-0 shoot maturation medium containing 300 mg/liter carbenicillin and 45 mg/liter glyphosate for two weeks; and shoots were transferred to B5 root induction medium containing 45 mg/l glyphosate. Rooted green plantlets were transplanted to potting soil and acclimated to green house conditions. Plants were maintained in a greenhouse under standard conditions. Developing seed was harvested at various stages after pollination and stored at −70° C. Mature seed was collected and stored under controlled conditions consisting of about 17° C. and 30% humidity.

GUS activity was qualitatively and quantitatively measured using methods known to those skilled in the art. In the qualitative analysis, plant tissue samples were collected from the roots, stems, leaves, flowers and developing pods. For the quantitative analysis, tissues were obtained from whole isolated seeds.

For qualitative GUS analysis, whole tissue sections were incubated with the GUS staining solution X-Gluc (5-bromo-4-chloro-3-indolyl-β-glucuronide) (1 milligram/milliliter) for an appropriate length of time, rinsed, and visually inspected for blue staining. For all three constructs, GUS expression was not observed in the roots, leaves, or stems of the transformed canola plants. Plants transformed with either the short e-napin (pMON72629) promoter or long e-napin (pMON72630) promoter demonstrated expression in the seed, while all but one event transformed with the native napin (pMON82357) promoter showed no expression in the seed. In the qualitative analysis, seed expression was determined by viewing GUS staining of the seed through the developing pods. Visible staining may not have been intense enough in the native napin promoter constructs to view seed expression through the pod tissues. Qualitative GUS analysis results are described in Table 1 below. Non-transformed canola plants were used as a negative control for comparison.

TABLE 1

Qualitative GUS Expression Analysis for Transformed Canola Events

| | Observed Staining |
|---|---|
| pMON82357 | |
| Event 1 | Septum, Funiculus |
| Event 2 | Septum, Funiculus |
| Event 3 | Septum, Funiculus, Silique Wall, |
| Event 4 | Septum, Funiculus, Stigma, |
| Event 5 | Septum, Funiculus |
| Event 6 | Septum, Funiculus |
| Event 7 | Septum, Funiculus |
| Event 8 | Septum, Funiculus, Filament, Nectarie |
| Event 9 | Septum, Funiculus, Filament, Nectarie |
| Event 10 | Septum, Funiculus |
| Event 11 | Septum, Funiculus, Nectarie |
| Event 12 | Septum, Funiculus |
| Event 13 | Septum, Funiculus, Seed (weakly stained) |
| pMON72629 | |
| Event 1 | Seed |
| Event 2 | Seed, Silique |
| Event 3 | Seed (weak), Inner Membrane |
| Event 4 | Seed, Inner Membrane and Cut Sites |
| Event 5 | Silique, Inner Membrane, Funiculus, Seed (all strong staining) |
| Event 6 | Seed |
| Event 7 | Inner Membrane (faint), 1 seed coat (weak) |
| Event 8 | Funiculus, maybe 1 seed |
| Event 9 | Silique (weak), Inner Membrane, Seed |
| Event 10 | Silique, Inner Membrane, Seed |
| Event 11 | Seed, Inner Membrane |
| Event 12 | Seed and Funiculus |
| Event 13 | Silique, Inner Membrane, Cut Sites, 1 cut Seed |
| Event 14 | none |
| Event 15 | Seed, slight Inner Membrane |
| pMON72630 | |
| Event 1 | none |
| Event 2 | Silique and Seed |
| Event 3 | Cut Sites, Funiculus, Seed (very weak) |
| Event 4 | Funiculus |
| Event 5 | Seed, slight Silique |
| Event 6 | Silique and Seed (weak) |
| Event 7 | Seed and Inner Membrane |
| Event 8 | Seed, Funiculus, Inner Membrane |
| Event 9 | Seed, Inner Membrane (not in 2nd well of seeds alone) |
| Event 10 | Seed, Funiculus, Cut Site |
| Event 11 | Heavy in Seed, Silique, Inner Membrane |
| Event 12 | Inner Membrane, Seed, slight Silique |
| Event 13 | Seed |
| Event 14 | Seed, Funiculus, Cut Site |
| Event 15 | Seed, faint Inner Membrane |
| Event 16 | Faint Funiculus, Multiple seed blue at funiculus attachment point |
| Event 17 | Seed, Funiculus, Silique |
| Negative Controls | |
| Event C1 | none |
| Event C2 | none |
| Event C3 | none |
| Event C4 | none |
| Event C5 | none |
| Event C6 | none |
| Event C7 | none |
| Event C8 | none |

For quantitative analysis, total protein was extracted from the seed of transformed canola plants when the seeds were near or at maturity. One microgram of total protein was used with the fluorogenic substrate 4-methylumbelliferyl-β-D- glucuronide (MUG) in a total reaction volume of 50 microliters. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a FluoroMax®-3 spectrofluorometer with MicroMax Reader (Horiba Jobin Yvon, Inc., Edison, N.J.), with slit width set at excitation 2 nm and emission 3 nm. Table 2 below shows the GUS activity expressed as pmole of 4-MU/microliter. This data is also depicted in FIG. 1 (Average GUS activity in pmoles/microliter for each construct). Non-transformed canola plants were used as a negative control for comparison.

In the quantitative assay, expression of GUS in the seed can be observed in those events presented in the qualitative analysis in which seed expression appeared to be lacking or too low to be detected by visual inspection. This is likely due to several factors. The quantitative analysis only used seeds isolated from pods which were harvested at a later maturity stage than seeds within the pod in the qualitative analysis. In addition, the quantitative assay is more sensitive and does not rely on visual perception of the staining of the seed through the pod tissue. The sample used for the quantitative assay was comprised solely of seed tissue and hence detection of GUS activity within the seed would be more easily detected, even at levels that may not be easily perceived through visual inspection. The qualitative analysis however, provides a general overview of the expression profile that is derived when using either the native napin promoter or short e-napin promoter or long e-napin promoter.

GUS activity in the seed and seed-associated tissue extracts was on average higher when transgene expression was driven by the short e-napin (pMON72629) and long e-napin (pMON72630) promoter than when driven by the native napin (pMON82357) promoter. GUS activity on average for the short e-napin promoter (SEQ ID NO:1) was 75.38 pmole/ml; GUS activity on average for the long e-napin promoter (SEQ ID NO:2) was 58.92 pmole/ml; and GUS activity on average for the native napin promoter (SEQ ID NO:7) was 37.94 pmole/ml. The short e-napin promoter thus gave a 1.98 fold increase in GUS activity over the native napin promoter, and the long e-napin promoter gave a 1.55 fold increase in GUS activity over the native napin promoter.

TABLE 2

Quantitative GUS Expression for Transformed Canola Events

| Construct | GUS Activity (pmole/ml) |
|---|---|
| PMON72629 Event 1 | 58.524 |
| PMON72629 Event 2 | 18.215 |
| PMON72629 Event 3 | 100.143 |
| PMON72629 Event 4 | 88.652 |
| PMON72629 Event 5 | 95.497 |
| PMON72629 Event 6 | 60.035 |
| PMON72629 Event 7 | 132.444 |
| PMON72629 Event 8 | 104.981 |
| PMON72629 Event 9 | 71.7 |
| PMON72629 Event 10 | 71.678 |
| PMON72629 Event 11 | 67.294 |
| PMON72629 Event 12 | 124.145 |
| PMON72629 Event 13 | 45.256 |
| PMON72629 Event 14 | <LOD |
| PMON72629 Event 15 | 92.261 |
| PMON72629 Average Expression | 75.38 |

TABLE 2-continued

Quantitative GUS Expression for Transformed Canola Events

| Construct | GUS Activity (pmole/ml) |
|---|---|
| PMON72630 Event 1 | <LOD |
| PMON72630 Event 2 | 93.264 |
| PMON72630 Event 3 | 29.879 |
| PMON72630 Event 4 | 49.689 |
| PMON72630 Event 5 | 86.641 |
| PMON72630 Event 6 | 57.212 |
| PMON72630 Event 7 | 54.619 |
| PMON72630 Event 8 | 50.099 |
| PMON72630 Event 9 | 15.057 |
| PMON72630 Event 10 | 24.564 |
| PMON72630 Event 11 | 131.072 |
| PMON72630 Event 12 | 88.762 |
| PMON72630 Event 13 | 23.959 |
| PMON72630 Event 14 | 81.494 |
| PMON72630 Event 15 | 103.698 |
| PMON72630 Event 16 | 19.339 |
| PMON72630 Event 17 | 92.248 |
| PMON72630 Average Expression | 58.92 |
| PMON82357 Event 1 | 0.257 |
| PMON82357 Event 2 | 47.421 |
| PMON82357 Event 3 | 75.546 |
| PMON82357 Event 4 | 50.387 |
| PMON82357 Event 5 | 38.605 |
| PMON82357 Event 6 | 39.544 |
| PMON82357 Event 7 | 14.416 |
| PMON82357 Event 8 | 23.487 |
| PMON82357 Event 9 | 37.720 |
| PMON82357 Event 10 | 123.013 |
| PMON82357 Event 11 | 6.425 |
| PMON82357 Event 12 | 21.058 |
| PMON82357 Event 13 | 15.393 |
| PMON82357 Average Expression | 37.94 |
| Negative Control Event C1 | 56.545 |
| Negative Control Event C2 | <LOD |
| Negative Control Event C3 | <LOD |
| Negative Control Event C4 | <LOD |
| Negative Control Event C5 | <LOD |
| Negative Control Event C6 | <LOD |
| Negative Control Event C7 | 18.999 |
| Negative Control Event C8 | <LOD |
| Negative Control Average Expression | 9.44 |

Example 3

Agronomic Trait Analysis

The enhanced napin promoters were analyzed for their ability to drive expression of a gene of interest for an agronomic trait. Two constructs were engineered to contain an enhanced napin promoter driving expression of genes that are in the fatty acid biosynthetic pathway in order to introduce genes coding for the enzymes that would reduce levels of saturated fatty acids in the seeds.

Figure 2:
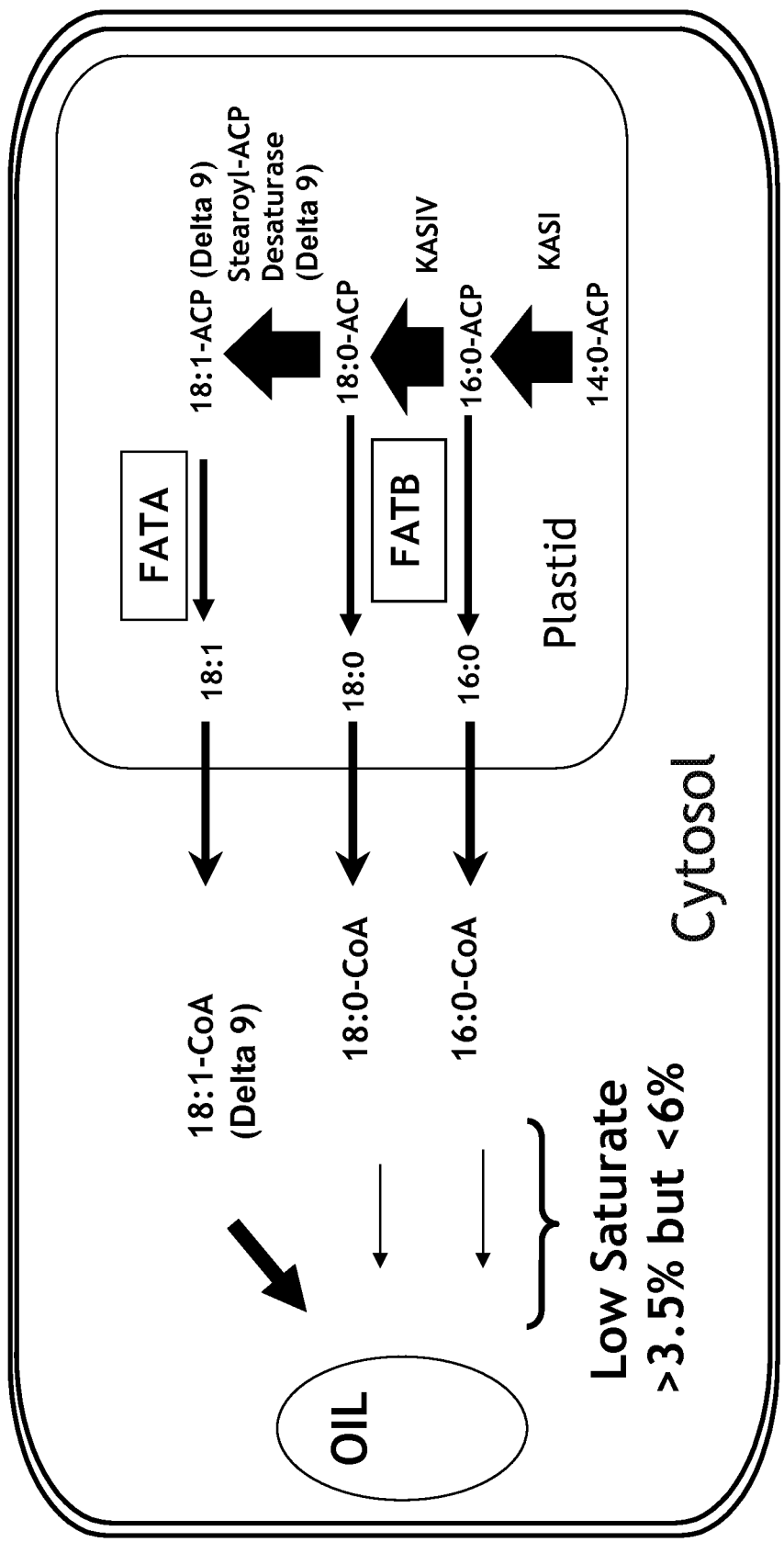
FIG. 2 illustrates schematically the fatty acid biosynthesis pathway in plants.

Fatty acid biosynthesis takes place in the plastid of the plant cell where the KAS enzymes (β-ketoacyl-acyl synthases) are the rate limiting enzymes that catalyze the conversion of the growing fatty acid (FA) chain. KAS I catalyzes conversion to palmitic acid and KAS IV catalyzes conversion to stearic acid. Delta 9-desaturase converts stearic acid to oleic acid. The growing FA chain is attached to an acyl carrier protein (ACP), which is then removed by one of 2 thioesterases, either FAT B or FAT A, prior to export of the FA into the cytosol. Here a CoA moiety attaches to the FA which eventually is incorporated into the triacylglycerol (TAG) backbone to form oil bodies. FIG. 2 depicts this pathway diagrammatically.

Figure 3:
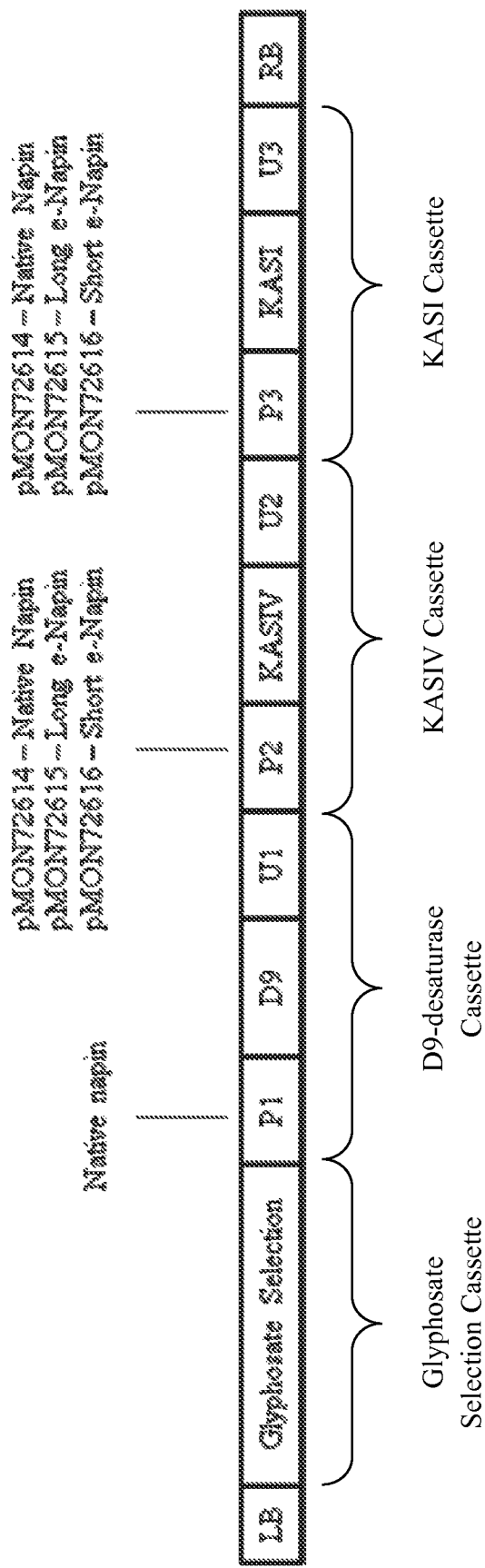
FIG. 3 illustrates schematically the constructs used for analyzing the chimeric promoters driving expression of fatty acid biosynthesis enzymes. These constructs contain four coding sequences, each with its own operably linked regulatory elements. The left border sequence is indicated as "LB"; a selection cassette for glyphosate tolerance is indicated as "Glyphosate Selection Cassette"; a cassette for expression of the D9-desaturase enzyme containing the native napin promoter (indicated as "P1"), operably linked to the D9-desaturase coding sequence (indicated as "D9"), operably linked to the native napin 3' UTR (indicated as "U1") is indicated as "D9-desaturase Cassette"; a KASIV cassette for the expression of the KASIV enzyme containing either the native napin promoter (pMON72614), the long e-napin promoter (pMON72615), or the short e-napin promoter (pMON72616) each indicated as "P2", operably linked to the KASIV coding sequence (indicated as "KASIV"), operably linked to the native napin 3' UTR (indicated as "U2") is indicated as "KASIV Cassette"; a KASI cassette for the expression of the KASI enzyme containing either the native napin promoter (pMON72614), the long e-napin promoter (pMON72615), or the short e-napin promoter (pMON72616) indicated as "P3", operably linked to the KASI coding sequence (indicated as KASI), operably linked to the native napin 3' UTR (indicated as "U3") is indicated as "KASI Cassette"; and the right border sequence is indicated as "RB".

The two genes that encode the fatty acid biosynthetic enzymes ketoacyl-acyl-synthases, KAS I and KAS IV from the genus *Cuphea pulcherrima*, (PCT Publication WO1998/46776), and a third gene, Delta-9-Desaturase from Castor bean (*Ricinus communis*, U.S. Pat. No. 5,723,595), were operably linked with the napin promoter, the short e-napin promoter, or the long e-napin promoter in plant transformation constructs. FIG. 3 depicts the arrangement of pMON72614, pMON72615, and pMON72616. These constructs contain four coding sequences, each with its own operably linked regulatory elements. The left border sequence is indicated as "LB"; a selection cassette for glyphosate tolerance is indicated as "Glyphosate Selection Cassette"; a cassette for expression of the D9-desaturase enzyme containing the native napin promoter (indicated as "P1"), operably linked to the D9-desaturase coding sequence (indicated as "D9"), operably linked to the native napin 3' UTR (indicated as "U1") is indicated as "D9-desaturase Cassette"; a KASIV cassette for the expression of the KASIV enzyme containing either the native napin promoter (pMON72614), the long e-napin promoter (pMON72615), or the short e-napin promoter (pMON72616) each indicated as "P2", operably linked to the KASIV coding sequence (indicated as "KASIV"), operably linked to the native napin 3' UTR (indicated as "U2") is indicated as "KASIV Cassette"; a KASI cassette for the expression of the KASI enzyme containing either the native napin promoter (pMON72614), the long e-napin promoter (pMON72615), or the short e-napin promoter (pMON72616) indicated as "P3", operably linked to the KASI coding sequence (indicated as KASI), operably linked to the native napin 3' UTR (indicated as "U3") is indicated as "KASI Cassette"; and the right border sequence is indicated as "RB".

These constructs were used to transform canola plants as described above. One hundred events of transformed canola plants were generated for each construct. Gene and molecular analysis for the presence of each gene of interest and the selectable marker was conducted. Events that were positive for both gene of interest and the selectable marker and that had one copy of the selectable marker were grown in a greenhouse. R1 seed was collected at maturity and 20 single seeds per event were analyzed by fatty acid methyl ester FAME/GC for fatty acid composition.

Plants from six events transformed with the construct containing the long e-napin promoter driving the KAS I and KAS IV genes (pMON72615) exhibited saturate levels below 5%. These plants were single copy for the selectable marker, and therefore single copy for the genes of interest, and segregated in a 3:1 distribution pattern. Plants from three events transformed with the construct containing the short e-napin promoter driving the KAS I and KAS IV genes (pMON72614) exhibited saturate levels below 5%. These plants were single copy for the selectable marker, and therefore single copy for the genes of interest, and segregated in a 3:1 distribution pattern. Plants from six events transformed with the construct containing the native napin promoter driving the KAS I and KAS IV genes (pMON72616) exhibited saturate levels below 5%. These plants were single copy for the selectable marker, and therefore single copy for the genes of interest, and segregated in a 3:1 distribution pattern.

All of these events germinated and were carried forward. Seed from the transformed canola plants was analyzed for 16:0 and 18:0 saturated fatty acid content to determine the saturate levels. A low saturate phenotype was defined as >3.5% but <6% of combined levels of 16:0+18:0 saturated fatty acids. A very low saturate phenotype also known as a "zero saturate phenotype" was defined as <3.5% combined levels of 16:0+18:0 saturated fatty acids. Data is provided in Table 3 below. Non-transformed canola plants were used as a negative control for comparison.

Saturate levels in the canola seed were on average higher when the KAS I and KAS IV genes were driven by the native napin promoter (pMON72614) than when driven by the long e-napin promoter (pMON72615) or the short e-napin promoter (pMON72616). The combined levels of 16:0+18:0 fatty acids (SUM) when the native napin promoter (pMON72614) was driving expression of the KAS I and KAS IV genes was on average 4.96%. The combined levels of 16:0+18:0 fatty acids (SUM) when the long e-napin promoter (pMON72615) was driving expression of the KAS I and KAS IV genes was on average 4.52%. The combined levels of 16:0+18:0 fatty acids (SUM) when the short e-napin promoter (pMON72616) was driving expression of the KAS I and KAS IV genes was on average 4.68%. The long e-napin promoter thus gave a 8.8% decrease in the combined levels of 16:0+18:0 fatty acids over the native napin promoter, and the short e-napin promoter gave a 5.6% decrease in the combined levels of 16:0+18:0 fatty acids over the native napin promoter. Some multicopy-gene insertion events, arising from transformations with either pMON72614, pMON72615, or pMON71616 demonstrated a zero saturation phenotype. The zero saturate phenotype in these events was possibly due to the additive effects of having multiple copies of the KAS I and KAS IV coding sequence expressed in the seed, but a larger population plants could be screened to identify a single-copy, zero saturate phenotype event.

TABLE 3

Saturate levels in canola plants

| Construct and Event | 16:0 (%) | 18:0 (%) | SUM (%) |
|---|---|---|---|
| pMON72614 (napin promoter) | | | |
| BN_G9304 | 2.69 | 1.83 | 4.52 |
| BN_G9221 | 2.9 | 1.9 | 4.8 |
| BN_G9483 | 3.19 | 1.63 | 4.82 |
| BN_G9299 | 2.8 | 2.87 | 5.67 |
| BN_G9466 | 3.63 | 1.39 | 5.02 |
| pMON72615 (long e-napin promoter) | | | |
| BN_G10337 | 2.99 | 1.21 | 4.2 |
| BN_G9343 | 2.8 | 1.22 | 4.02 |
| BN_G9394 | 3.47 | 1.16 | 4.63 |
| BN_G9386 | 3.15 | 1.51 | 4.66 |
| BN_G9762 | 3.41 | 1.38 | 4.79 |
| BN_G10769 | 3.48 | 1.38 | 4.86 |
| pMON72616 (short e-napin promoter) | | | |
| BN_G9588 | 3.62 | 0.94 | 4.56 |
| BN_G9593 | 3.55 | 1.09 | 4.64 |
| BN_G9396 | 3.35 | 1.3 | 4.65 |
| BN_G11616 | 3.12 | 1.61 | 4.73 |
| BN_G1162 | 3.24 | 1.51 | 4.75 |
| BN_G9595 | 3.56 | 1.23 | 4.79 |
| Non-transgenic control | | | |
| SP30052:0808 | 4.37 | 1.63 | 6 |
| SP30052:0809 | 4.49 | 1.55 | 6.04 |
| SP30052:0810 | 5.65 | 1.87 | 7.52 |

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

The invention claimed is:

1. A chimeric promoter comprising a first DNA molecule combined with a second DNA molecule, wherein said first DNA molecule is a native napin promoter comprising a sequence selected from the group consisting of SEQ ID NOs: 6, 7, 8, 9, 10, 11, 12, 13, 14, 15, 16, and 17 and said second DNA molecule comprises SEQ ID NO:19, wherein said first DNA molecule and said second DNA molecule are a heterologous combination, and wherein the chimeric promoter has increased seed expression compared to said native napin promoter.

2. A chimeric promoter comprising a first DNA molecule and a second DNA molecule, wherein said first DNA molecule is a native napin promoter and said second DNA molecule comprises SEQ ID NO:19, wherein said first DNA molecule and said second DNA molecule are a heterologous combination, wherein the chimeric promoter has increased seed expression compared to the native napin promoter, and wherein said chimeric promoter has gene regulatory activity and a DNA sequence with at least 97 percent identity to SEQ ID NO:1.

3. The chimeric promoter of claim 2, wherein said chimeric promoter has gene regulatory activity and a DNA sequence with at least 99 percent identity SEQ ID NO:1.

4. The chimeric promoter of claim 2, wherein said chimeric promoter comprises the DNA sequence of SEQ ID NO:1.

5. A DNA construct comprising the chimeric promoter of claim 1, and wherein said chimeric promoter is operably linked to a heterologous transcribable polynucleotide molecule.

6. The DNA construct of claim 5, wherein said chimeric promoter comprises the DNA sequence of SEQ ID NO: 1.

7. The DNA construct of claim 5, wherein the transcribable polynucleotide molecule is a gene of agronomic interest.

8. The DNA construct of claim 7, wherein the gene of agronomic interest is capable of providing a modified oil composition.

9. A transgenic plant cell comprising the DNA construct of claim 5.

10. The transgenic plant cell of claim 9, wherein said transgenic plant cell is a dicotyledonous plant cell.

11. The transgenic plant cell of claim 10, wherein said transgenic plant cell is selected from the group consisting of tobacco plant cell, tomato plant cell, potato plant cell, soybean plant cell, cotton plant cell, canola plant cell, sunflower plant cell and alfalfa plant cell.

12. A transgenic plant comprising the chimeric promoter of claim 1.

* * * * *